US011376422B2

(12) United States Patent
Gross

(10) Patent No.: US 11,376,422 B2
(45) Date of Patent: *Jul. 5, 2022

(54) ELECTRICAL TREATMENT OF ALZHEIMER'S DISEASE

(71) Applicant: RAINBOW MEDICAL LTD., Herzeliyah (IL)

(72) Inventor: Yossi Gross, Moshav Mazor (IL)

(73) Assignee: RAINBOW MEDICAL LTD., Herzliya (IL)

(*) Notice: Subject to any disclaimer, the term of this patent is extended or adjusted under 35 U.S.C. 154(b) by 297 days.

This patent is subject to a terminal disclaimer.

(21) Appl. No.: 16/692,528

(22) Filed: Nov. 22, 2019

(65) Prior Publication Data
US 2020/0108245 A1 Apr. 9, 2020

Related U.S. Application Data

(63) Continuation of application No. 15/742,245, filed as application No. PCT/IL2016/050728 on Jul. 7, 2016, (Continued)

(51) Int. Cl.
*A61N 1/05* (2006.01)
*A61N 1/30* (2006.01)
(Continued)

(52) U.S. Cl.
CPC ............. *A61N 1/0529* (2013.01); *A61N 1/20* (2013.01); *A61N 1/30* (2013.01); *A61N 1/325* (2013.01); *A61N 1/36025* (2013.01)

(58) Field of Classification Search
None
See application file for complete search history.

(56) References Cited

U.S. PATENT DOCUMENTS 4,044,774 A 8/1977 Corbin et al.
4,503,863 A 3/1985 Katims
(Continued)

FOREIGN PATENT DOCUMENTS

JP 2004-321242 11/2004
JP 2007-501067 1/2007
(Continued)

OTHER PUBLICATIONS

Karran E et al., 1 "The Amyloid cascade hypothesis for Alzheimer's disease: an appraisal for the development of therapeutics," Nature Reviews Drug Discovery, vol. 10; 698-712, Sep. 2011.
(Continued)

*Primary Examiner* — Ankit D Tejani
(74) *Attorney, Agent, or Firm* — Sughrue Mion, PLLC

(57) ABSTRACT

An electrical amyloid beta-clearance system for treating a subject identified as at risk of or suffering from Alzheimer's disease is provided, the system including midplane treatment electrodes, adapted to be disposed over a superior sagittal sinus, outside and in electrical contact with a skull of a head of the subject; lateral treatment electrodes, adapted to be disposed between 1 and 12 cm of a sagittal midplane of the skull; and control circuitry, configured to clear amyloid beta from a subarachnoid space to the superior sagittal sinus, by applying one or more treatment currents between (a) one or more of the midplane treatment electrodes and (b) one or more of the lateral treatment electrodes. Other embodiments are also described.

34 Claims, 5 Drawing Sheets

Related U.S. Application Data now Pat. No. 10,532,204, which is a continuation-in-part of application No. 14/794,739, filed on Jul. 8, 2015, now Pat. No. 9,616,221.

(51) Int. Cl.
  *A61N 1/32* (2006.01)
  *A61N 1/36* (2006.01)
  *A61N 1/20* (2006.01)

(56) References Cited

U.S. PATENT DOCUMENTS

| | | |
|---|---|---|
| 5,088,977 A | 2/1992 | Sibalis |
| 5,121,754 A | 6/1992 | Mullett |
| 5,433,739 A | 7/1995 | Sluijter et al. |
| 5,529,574 A | 6/1996 | Frackelton |
| 5,792,100 A | 8/1998 | Shantha |
| 5,911,223 A | 6/1999 | Weaver et al. |
| 5,938,690 A | 8/1999 | Law et al. |
| 6,041,252 A | 3/2000 | Walker et al. |
| 6,146,380 A | 11/2000 | Racz et al. |
| 6,161,047 A | 12/2000 | King et al. |
| 6,360,750 B1 | 3/2002 | Gerber et al. |
| 6,567,702 B1 | 5/2003 | Nekhendzy et al. |
| 6,591,138 B1 | 7/2003 | Fischell et al. |
| 6,602,248 B1 | 8/2003 | Sharps et al. |
| 6,620,155 B2 | 9/2003 | Underwood et al. |
| 6,941,172 B2 | 9/2005 | Nachum |
| 6,997,941 B2 | 2/2006 | Sharkey et al. |
| 7,013,177 B1 | 3/2006 | Whitehurst et al. |
| 7,120,489 B2 | 10/2006 | Shalev et al. |
| 7,217,351 B2 | 5/2007 | Krumme |
| 7,223,227 B2 | 5/2007 | Pflueger |
| 7,270,659 B2 | 9/2007 | Ricart et al. |
| 7,317,947 B2 | 1/2008 | Wahlstrand et al. |
| 7,398,121 B2 | 7/2008 | Matsumura et al. |
| 7,509,171 B2 | 3/2009 | DiMauro |
| 7,640,062 B2 | 12/2009 | Shalev |
| 7,818,063 B2 | 10/2010 | Wallace et al. |
| 7,831,306 B2 | 11/2010 | Finch et al. |
| 7,860,569 B2 | 12/2010 | Solberg et al. |
| 8,060,207 B2 | 11/2011 | Wallace et al. |
| 8,103,350 B2 | 1/2012 | Wallace et al. |
| 8,190,248 B2 | 5/2012 | Besio et al. |
| 8,353,853 B1 | 1/2013 | Kyle et al. |
| 8,457,761 B2 | 6/2013 | Wariar |
| 8,577,469 B2 | 11/2013 | Gross |
| 8,676,348 B2 | 3/2014 | Gross |
| 8,731,674 B2 | 5/2014 | Wallace et al. |
| 9,616,221 B2 | 4/2017 | Gross |
| 9,724,513 B2 | 8/2017 | Lane et al. |
| 9,724,515 B2 | 8/2017 | Fostick et al. |
| 9,731,122 B2 | 8/2017 | Gross |
| 9,775,996 B2 * | 10/2017 | Gross ............ A61N 1/20 |
| 10,398,884 B2 | 9/2019 | Lad et al. |
| 10,532,204 B2 | 1/2020 | Gross |
| 2002/0151948 A1 | 10/2002 | King et al. |
| 2002/0183683 A1 | 12/2002 | Lerner |
| 2003/0130707 A1 | 7/2003 | Gan et al. |
| 2003/0158589 A1 | 8/2003 | Katsnelson |
| 2003/0216792 A1 | 11/2003 | Levin et al. |
| 2003/0225331 A1 | 12/2003 | Diederich et al. |
| 2004/0002746 A1 | 1/2004 | Ryan et al. |
| 2004/0019381 A1 | 1/2004 | Pflueger |
| 2004/0049180 A1 | 3/2004 | Sharps et al. |
| 2004/0116977 A1 | 6/2004 | Finch et al. |
| 2004/0210209 A1 | 10/2004 | Yeung et al. |
| 2005/0010205 A1 | 1/2005 | Hovda et al. |
| 2005/0021104 A1 | 1/2005 | DiLorenzo |
| 2005/0119650 A1 | 6/2005 | Sanders et al. |
| 2005/0137646 A1 | 6/2005 | Wallace et al. |
| 2005/0137647 A1 | 6/2005 | Wallace et al. |
| 2005/0159790 A1 | 7/2005 | Shalev |
| 2005/0187589 A1 | 8/2005 | Wallace et al. |
| 2005/0203599 A1 | 9/2005 | Garabedian et al. |
| 2005/0203600 A1 | 9/2005 | Wallace et al. |
| 2005/0203602 A1 | 9/2005 | Wallace et al. |
| 2005/0222647 A1 | 10/2005 | Wahlstrand et al. |
| 2005/0277996 A1 | 12/2005 | Podhajsky et al. |
| 2006/0030895 A1 | 2/2006 | Simon et al. |
| 2006/0106430 A1 | 5/2006 | Fowler et al. |
| 2006/0224223 A1 | 10/2006 | Podhajsky et al. |
| 2006/0293723 A1 | 12/2006 | Whitehurst et al. |
| 2007/0000784 A1 | 1/2007 | Paul et al. |
| 2007/0073402 A1 | 3/2007 | Vresilovic et al. |
| 2007/0162086 A1 | 7/2007 | Dilorenzo |
| 2007/0213700 A1 | 9/2007 | Davison et al. |
| 2007/0233202 A1 | 10/2007 | Wallace et al. |
| 2007/0255338 A1 | 11/2007 | Wahlstrand |
| 2008/0009927 A1 | 1/2008 | Vilims |
| 2008/0033503 A1 | 2/2008 | Fowler et al. |
| 2008/0119907 A1 | 5/2008 | Stahmann |
| 2008/0260542 A1 | 10/2008 | Nishikawa et al. |
| 2009/0112278 A1 | 4/2009 | Wingeier et al. |
| 2009/0125080 A1 | 5/2009 | Montgomery |
| 2009/0126813 A1 | 5/2009 | Yanagisawa et al. |
| 2009/0131850 A1 | 5/2009 | Geiger |
| 2009/0312816 A1 | 12/2009 | Gross |
| 2010/0217369 A1 | 8/2010 | Gross |
| 2010/0324441 A1 | 12/2010 | Hargrove et al. |
| 2011/0046540 A1 | 2/2011 | Alterman et al. |
| 2011/0054518 A1 | 3/2011 | Carbunaru et al. |
| 2011/0160638 A1 | 6/2011 | Mauge et al. |
| 2011/0160797 A1 | 6/2011 | Makous et al. |
| 2012/0053659 A1 | 3/2012 | Molnar et al. |
| 2012/0203307 A1 | 8/2012 | Schroeppel et al. |
| 2013/0066392 A1 | 3/2013 | Simon et al. |
| 2013/0102952 A1 | 4/2013 | Gross |
| 2013/0166006 A1 | 6/2013 | Williams |
| 2013/0289385 A1 | 10/2013 | Lozano et al. |
| 2014/0058189 A1 | 2/2014 | Stubbeman |
| 2014/0088672 A1 | 3/2014 | Bedenbaugh |
| 2014/0207224 A1 | 7/2014 | Simon |
| 2014/0257168 A1 | 9/2014 | Gill |
| 2014/0324128 A1 | 10/2014 | Gross |
| 2015/0011927 A1 | 1/2015 | Hua |
| 2015/0119898 A1 | 4/2015 | Desalles et al. |
| 2016/0331970 A1 | 11/2016 | Lozano |
| 2017/0007823 A1 | 1/2017 | Gross |
| 2017/0056642 A1 | 3/2017 | Moffitt et al. |
| 2017/0120053 A1 | 5/2017 | Fostick et al. |
| 2017/0182317 A1 | 6/2017 | Gross et al. |
| 2017/0296821 A1 | 10/2017 | Fostick et al. |
| 2018/0071523 A1 | 3/2018 | Gross et al. |
| 2018/0193633 A1 | 7/2018 | Gross |
| 2018/0193646 A1 | 7/2018 | Fostick et al. |
| 2018/0318575 A1 | 11/2018 | Gross et al. |

FOREIGN PATENT DOCUMENTS

| | | |
|---|---|---|
| WO | 94/05369 | 3/1994 |
| WO | 01/52931 | 7/2001 |
| WO | 01/85027 | 11/2001 |
| WO | 2001/085094 | 11/2001 |
| WO | 2005/011805 | 2/2005 |
| WO | 2006/090397 | 8/2006 |
| WO | 2008/007369 | 1/2008 |
| WO | 2017/006327 | 1/2017 |
| WO | 2017/072769 | 5/2017 |
| WO | 2017/115351 | 7/2017 |
| WO | 2018/051338 | 3/2018 |

OTHER PUBLICATIONS

De La Torre JC, "Vascular Basis of Alzheimer's Pathogensis," Ann NY Acad Sci. 977:196-215 (Nov. 2002).
Weller RO et al, "Perivascular Drainage of Amyloid-b Peptides from the Brain and Its Failure in Cerebral Amyloid Angiopathy and Alzheimer's Disease," Brain Pathology Apr. 18, 2008 253-266.
Brief PubMed search for metal ions in Alzheimers.
An Office Action dated Sep. 27, 2016, which issued during the prosecution of U.S. Appl. No. 14/926,705.
U.S. Appl. No. 62/642,663, filed Mar. 14, 2018.

(56) References Cited

OTHER PUBLICATIONS

An International Search Report and a Written Opinion both dated Aug. 7, 2008, which issued during the prosecution of Applicant's PCT/IL2007/000865.
An Office Action dated Mar. 29, 2013, which issued during the prosecution of U.S. Appl. No. 12/373,306.
An Office Action dated Oct. 31, 2011, which issued during the prosecution of U.S. Appl. No. 12/373,306.
An Office Action dated Oct. 1, 2012, which issued during the prosecution of U.S. Appl. No. 12/373,306.
Notice of Allowance dated U.S. Appl. No. Jul. 24, 2013, which issued during the prosecution of U.S. Appl. No. 12/373,306.
An Office Action dated Apr. 11, 2013, which issued during the prosecution of U.S. Appl. No. 13/663,757.
Notice of Allowance dated Oct. 28, 2013, which issued during the prosecution of U.S. Appl. No. 13/663,757.
Elixmann IM et al., "In-vitro evaluation of a drainage catheter with integrated bioimpedance electrodes to determine ventricular size," Biomed Tech 2013; 58 (Suppl. 1) Sep. 2013 (2 pages total).
An Office Action dated Aug. 31, 2015, which issued during the prosecution of U.S. Appl. No. 13/872,794.
An Applicant Initiated Interview Summary dated Dec. 14, 2015, which issued during the prosecution of U.S. Appl. No. 13/872,794.
An Office Action dated Feb. 3, 2016, which issued during the prosecution of U.S. Appl. No. 13/872,794.
Notice of Allowance dated Dec. 9, 2016, which issued during the prosecution of U.S. Appl. No. 14/794,739.
An Applicant Initiated Interview Summary dated Feb. 25, 2016, which issued during the prosecution of U.S. Appl. No. 13/872,794.
An Office Action dated Jun. 15, 2016, which issued during the prosecution of U.S. Appl. No. 13/872,794.
An International Search Report and a Written Opinion both dated Oct. 20, 2016, which issued during the prosecution of Applicant's PCT/IL2016/050728.
An Office Action dated Sep. 21, 2016, which issued during the prosecution of U.S. Appl. No. 14/794,739.
An International Search Report and a Written Opinion both dated Jan. 26, 2017, the prosecution of Applicant's PCT/IL2016/051161.
Notice of Allowance dated Jul. 14, 2017, which issued during the prosecution of U.S. Appl. No. 13/872,794.
An Office Action dated May 26, 2017, which issued during the prosecution of U.S. Appl. No. 15/453,290.
An International Preliminary Report on Patentability dated Apr. 7, 2009, which issued during the prosecution of Applicant's PCT/IL2007/000865.
Loutzenhiser, "Membrane Potential measurements in renal afferent and efferent arterioles: actions of Angiotensin II", AJP-Renal Physiol Aug. 1, 1997 vol. 273 No. 2 F307-F314.
U.S. Appl. No. 60/830,717, filed Jul. 12, 2006.
Dao-Sheng Liu et al., "Activation of Na+ and K+ Pumping Modes of (Na,K)—ATPase by an Oscillating Electric Field," The Journal of Biological Chemistry, vol. 265. No. 13, May 5, 1990. (pp. 7260-7267).
Robert F. Service.. "Electric fields deliver drugs into tumors." http://news.sciencemaa.ora. Feb. 4, 2015. (5 Pages Total).
Vernengo J, "Injectable Bioadhesive Hydrogels for Nucleus Pulposus Replacement and Repair of the Damaged Intervertebral Disc: A Thesis," Drexel University (Jan. 2007).
Urban JPG et al., "The nucleus of the intervertebral disc from development to degeneration," American Zoologist 40(1): 53-61 (2000).
Cheung KMC et al., "Intervertebral disc regeneration by use of autologous mesenchymal stem cells, an experimental model in rabbits," Abstract from the SRS 2004 Annual Meeting.
Freemont TJ et al., "Degeneration of intervertebral discs: current understanding of cellular and molecular events, and implications for novel therapies," Expert Reviews in Molecular Biology, Mar. 29, 2001 (Cambridge University Press).

An Office Action dated Sep. 12, 2011, which issued during the prosecution of U.S. Appl. No. 12/373,306.
An Office Action dated Jul. 24, 2017, which issued during the prosecution of U.S. Appl. No. 14/982,187.
An International Search Report and a Written Opinion both dated Mar. 10, 2017, which issued during the prosecution of Applicant's PCT/IL2016/051363.
An Office Action dated Apr. 25, 2018, which issued during the prosecution of U.S. Appl. No. 15/637,330.
U.S. Appl. No. 62/444,939, filed Jan. 11, 2017.
An Office Action dated Jul. 10, 2019, which issued during the prosecution of U.S. Appl. No. 15/864,065.
An International Search Report and a Written Opinion both dated May 23, 2019, which issued during the prosecution of Applicant's PCT/IL2019/050284.
An Office Action dated Mar. 25, 2019, which issued during the prosecution of U.S. Appl. No. 15/742,245.
Borlase NM, "The thalamus in Parkinson's Disease," Department of Psychology, University of Canterbury, 2012.
Fernandes J, "Protein May Prevent Neuron Death in Huntington's Patients, Study Finds," huntingtonsdiseasenews.com, Jan. 19, 2017.
Lee H-J, "Extracellular asynuclein a novel and crucial factor in Lewy body diseases," Nat. Rev. Neurol. 10, 92-98 (Feb. 2014); published online Jan. 28, 2014.
Starr PA et al., "Parkinson's Disease FAQ—Deep Brain Stimulation for Parkinson's Disease," UCSF Apr. 19, 2017.
Perez RG et al., "A Role for Alpha-Synuclein in the Regulation of Dopamine Biosynthesis," The Journal of Neuroscience, Apr. 15, 2002, 22(8):3090-3099.
Breydo L et al., "α-Synuclein misfolding and Parkinson's disease," Biochimica et Biophysica Acta 1822 (2012) 261-285 (Available online Oct. 12, 2011).
Deleidi M et al., "Protein Clearance Mechanisms of Alpha-Synuclein and Amyloid-Beta in Lewy Body Disorders," International Journal of Alzheimer's Disease, vol. 2012.
Xie L et al., "Sleep Drives Metabolite Clearance from the Adult Brain," Science. Oct. 18, 2013; 342(6156).
Valdinocci D et al., "Potential Modes of Intercellular α-Synuclein Transmission," International Journal of Molecular Sciences, Feb. 22, 2017.
U.S. Appl. No. 62/500,747, filed May 3, 2017.
An Office Action dated Jul. 29, 2019, which issued during the prosecution of U.S. Appl. No. 15/618,325.
Sawyer, P N et al. "Measurement of streaming potentials of mammalian blood vessels, aorta and vena cava, in vivo." Biophysical journal vol. 6,5 (1966): 641-51. doi:10.1016/50006-3495(66)86683-3, https://www.ncbi.nlm.nih.gov/pmc/articles/PMC1368020/, viewed on Jul. 22, 2019.
An Office Action dated Nov. 29, 2019, which issued during the prosecution of U.S. Appl. No. 15/969,411.
An Office Action dated Jan. 7, 2020, which issued during the prosecution of U.S. Appl. No. 15/618,325.
An Office Action dated Jan. 7, 2020, which issued during the prosecution of European Patent Application No. 16741703.9.
An Office Action dated Jan. 22, 2020, which issued during the prosecution of U.S. Appl. No. 15/771,551.
An Office Action dated Mar. 6, 2020, which issued during the prosecution of U.S. Appl. No. 15/618,325.
An Office Action together with the English translation dated Aug. 19, 2020, which issued during the prosecution of Japanese Patent Application No. 2018-521586.
An Office Action dated Mar. 30, 2020, which issued during the prosecution of U.S. Appl. No. 16/574,772.
An Office Action dated Nov. 20, 2020, which issued during the prosecution of U.S. Appl. No. 16/353,407.
An International Search Report and a Written Opinion both dated Dec. 20, 2020, which issued during the prosecution of Applicant's PCT/IL2020/051022.
An Office Action dated Nov. 4, 2021, which issued during the prosecution of U.S. Appl. No. 16/713,660.

* cited by examiner

ELECTRICAL TREATMENT OF ALZHEIMER'S DISEASE

CROSS-REFERENCE TO RELATED APPLICATIONS

The present application is a continuation of U.S. application Ser. No. 15/742,245, filed Jan. 5, 2018, now U.S. Pat. No. 10,532,204, which is the U.S. national stage of International Application PCT/IL2016/050728, filed Jul. 7, 2016, which claims priority from and is a continuation-in-part of U.S. application Ser. No. 14/794,739, filed Jul. 8, 2015, now U.S. Pat. No. 9,616,221, which is assigned to the assignee of the present application and is incorporated herein by reference.

FIELD OF THE APPLICATION

The present invention relates generally to treatment and prevention of Alzheimer's diseases, and specifically to electrical techniques for treating and preventing Alzheimer's disease.

BACKGROUND OF THE APPLICATION

Alzheimer's disease is a chronic neurodegenerative disease that causes dementia. Accumulation of amyloid beta in the brain is widely believed to contribute to the development of Alzheimer's disease.

SUMMARY OF THE APPLICATION

Some embodiments of the present invention provide a system and methods for treating Alzheimer's disease. The system comprises a plurality of midplane treatment electrodes, a plurality of lateral treatment electrodes, and control circuitry, which is electrically coupled to the treatment electrodes. For some applications, a method for treating Alzheimer's disease comprises:
disposing the midplane treatment electrodes over a superior sagittal sinus, outside and in electrical contact with a skull of a head of a subject identified as at risk of or suffering from Alzheimer's disease;
disposing the lateral treatment electrodes between 1 and 12 cm of a sagittal midplane of the skull; and
treating the subject by electroosmotically driving fluid and/or clearing amyloid beta from a subarachnoid space to the superior sagittal sinus, by activating the control circuitry to apply one or more treatment currents between (a) one or more of the midplane treatment electrodes and (b) one or more of the lateral treatment electrodes.

For some applications, treating the subject comprises facilitating clearance of amyloid beta from the subarachnoid space to the superior sagittal sinus by electroosmotically driving the fluid from the subarachnoid space to the superior sagittal sinus. Alternatively or additionally, for some applications, treating the subject comprises facilitating clearance of metal ions from the subarachnoid space to the superior sagittal sinus by electroosmotically driving the fluid from the subarachnoid space to the superior sagittal sinus.

Avoiding insertion of midplane treatment electrodes into the superior sagittal sinus may reduce any risks associated with implantation and operation of the system.

For some applications, the control circuitry is activated to configure the midplane treatment electrodes as cathodes, and the lateral treatment electrodes as anodes. This electrical polarity may electroosmotically drive fluid from the subarachnoid space to the superior sagittal sinus, which may treat (a) Alzheimer's disease and/or cerebral amyloid angiopathy (CAA) by clearing amyloid beta from the subarachnoid space to the superior sagittal sinus, and/or (b) hydrocephalus, by driving cerebrospinal fluid (CSF) out of the brain's ventricular system via subarachnoid space 50.

Alternatively, for some applications, the control circuitry is activated to configure the midplane treatment electrodes as anodes, and the lateral treatment electrodes as cathodes. This electrical polarity may electrophoretically drive amyloid beta from the subarachnoid space to the superior sagittal sinus, which may treat Alzheimer's disease and/or cerebral amyloid angiopathy (CAA) by clearing amyloid beta from the subarachnoid space to superior sagittal sinus.

For some applications, the control circuitry is activated to independently apply the treatment currents between respective pairs of the midplane and the lateral treatment electrodes.

For some applications, the one or more treatment currents applied using the midplane and the lateral treatment electrodes pass between the subarachnoid space and the superior sagittal sinus, via inferolateral surfaces of the superior sagittal sinus. For these applications, the locations of the midplane treatment electrodes and/or the lateral treatment electrodes are typically selected such that the one or more treatment currents pass through the inferolateral surfaces. For example, for configurations in which the lateral treatment electrodes are disposed outside and in electrical contact with the skull, the lateral treatment electrodes may be disposed between 5 and 12 cm of the sagittal midplane of the skull; for configurations in which the lateral treatment electrodes are implanted under an arachnoid mater of the subject, the lateral treatment electrodes may be disposed between 1 and 3 cm of the sagittal midplane of the skull.

For some applications, the midplane treatment electrodes are disposed outside the head, such as on an external surface of the head. For other applications, the midplane treatment electrodes are implanted under skin of the head. For some applications, the system further comprises a midplane lead, along which the midplane treatment electrodes are disposed (e.g., fixed).

For some applications, the lateral treatment electrodes are disposed outside and in electrical contact with the skull. For some of these applications, the lateral treatment electrodes are disposed outside the head, such as on the external surface of the head, or are implanted under the skin of the head.

For some applications, the lateral treatment electrodes comprise left lateral treatment electrodes and right lateral treatment electrodes. The left lateral treatment electrodes are disposed left of the sagittal midplane of the skull, and the right lateral treatment electrodes are disposed right of the sagittal midplane of the skull. For some applications, the control circuitry is activated to configure the midplane treatment electrodes as cathodes, and the left and the right lateral treatment electrodes as left and right anodes, respectively.

For some applications, the lateral treatment electrodes are implanted under arachnoid mater of the subject, such as in the subarachnoid space or in gray or white matter of a brain of the subject.

In some applications of the present invention, the techniques described herein are alternatively or additionally used to treat cerebral amyloid angiopathy (CAA).

In some applications of the present invention, the techniques described herein are alternatively or additionally used to treat hydrocephalus, by driving cerebrospinal fluid (CSF) out of the brain's ventricular system via the subarachnoid space.

There is therefore provided, in accordance with an inventive concept 1 of the present application, an electrical amyloid beta-clearance system for treating a subject identified as at risk of or suffering from Alzheimer's disease, the system including:

midplane treatment electrodes, adapted to be disposed over a superior sagittal sinus, outside and in electrical contact with a skull of a head of the subject;

lateral treatment electrodes, adapted to be disposed between 1 and 12 cm of a sagittal midplane of the skull; and control circuitry, configured to clear amyloid beta from a subarachnoid space to the superior sagittal sinus, by applying one or more treatment currents between (a) one or more of the midplane treatment electrodes and (b) one or more of the lateral treatment electrodes.

Inventive concept 2. The system according to inventive concept 1, wherein the control circuitry is configured to clear the amyloid beta by electroosmotically driving fluid from the subarachnoid space to the superior sagittal sinus.

Inventive concept 3. The system according to inventive concept 2, wherein the control circuitry is configured to configure the midplane treatment electrodes as cathodes, and the lateral treatment electrodes as anodes.

Inventive concept 4. The system according to inventive concept 2, wherein the lateral treatment electrodes include (a) left lateral treatment electrodes, which are adapted to be disposed left of the sagittal midplane of the skull, and (b) right lateral treatment electrodes, which are adapted to be disposed right of the sagittal midplane of the skull, and wherein the control circuitry is configured to configure the midplane treatment electrodes as cathodes, and the left and the right lateral treatment electrodes as left and right anodes, respectively.

Inventive concept 5. The system according to inventive concept 1, wherein the control circuitry is configured to clear the amyloid beta by electrophoretically driving the amyloid beta from the subarachnoid space to the superior sagittal sinus.

Inventive concept 6. The system according to inventive concept 5, wherein the control circuitry is configured to configure the midplane treatment electrodes as anodes, and the lateral treatment electrodes as cathodes.

Inventive concept 7. The system according to inventive concept 5, wherein the lateral treatment electrodes include (a) left lateral treatment electrodes, which are adapted to be disposed left of the sagittal midplane of the skull, and (b) right lateral treatment electrodes, which are adapted to be disposed right of the sagittal midplane of the skull, and wherein the control circuitry is configured to configure the midplane treatment electrodes as anodes, and the left and the right lateral treatment electrodes as left and right cathodes, respectively.

Inventive concept 8. The system according to inventive concept 1, wherein the control circuitry is configured to apply the one or more treatment currents with an average amplitude of between 1 and 3 milliamps.

Inventive concept 9. The system according to any one of inventive concepts 1-8, wherein the lateral treatment electrodes are adapted to be disposed outside and in electrical contact with the skull.

Inventive concept 10. The system according to inventive concept 9, wherein the lateral treatment electrodes are adapted to be disposed outside the head.

Inventive concept 11. The system according to inventive concept 10, wherein the lateral treatment electrodes are adapted to be disposed on an external surface of the head.

Inventive concept 12. The system according to inventive concept 9, wherein the lateral treatment electrodes are adapted to be implanted under skin of the head.

Inventive concept 13. The system according to any one of inventive concepts 1-8, wherein the midplane treatment electrodes are adapted to be disposed outside the head.

Inventive concept 14. The system according to inventive concept 13, wherein the midplane treatment electrodes are adapted to be disposed on an external surface of the head.

Inventive concept 15. The system according to any one of inventive concepts 1-8, wherein the midplane treatment electrodes are adapted to be implanted under skin of the head.

Inventive concept 16. The system according to any one of inventive concepts 1-8, wherein the lateral treatment electrodes are adapted to be implanted under an arachnoid mater of the subject.

Inventive concept 17. The system according to inventive concept 16, wherein the lateral treatment electrodes are adapted to be disposed in the subarachnoid space.

Inventive concept 18. The system according to inventive concept 16, wherein the lateral treatment electrodes are adapted to be disposed in gray or white matter of a brain of the subject.

Inventive concept 19. The system according to any one of inventive concepts 1-8, wherein the system further includes (a) a midplane lead, which is adapted to be disposed outside the skull, and (b) a lateral lead, which is adapted to be disposed within 1 and 12 cm of the sagittal midplane of the skull, wherein the system includes at least five midplane treatment electrodes that are disposed along the midplane lead, and wherein the system includes at least five lateral treatment electrodes that are disposed along the lateral lead.

Inventive concept 20. The system according to any one of inventive concepts 1-8, wherein the lateral treatment electrodes include:

left lateral treatment electrodes, which are adapted to be disposed left of the sagittal midplane of the skull; and right lateral treatment electrodes, which are adapted to be disposed right of the sagittal midplane of the skull.

Inventive concept 21. The system according to inventive concept 20, wherein the control circuitry is configured to apply the one or more treatment currents between (a) one or more of the midplane treatment electrodes and (b) one or more of the lateral treatment electrodes includes activating the control circuitry to apply:

a first treatment current between a first one of the midplane treatment electrodes and a first one of the left lateral treatment electrodes, a second treatment current between the first one of the midplane treatment electrodes and a first one of the right lateral treatment electrodes, a third treatment current between a second one of the midplane treatment electrodes and a second one of the left lateral treatment electrodes, and a fourth treatment current between the second one of the midplane treatment electrodes and a second one of the right lateral treatment electrodes.

Inventive concept 22. The system according to any one of inventive concepts 1-8, wherein the control circuitry is configured to:
detect a voltage difference between the subarachnoid space and the superior sagittal sinus, and
set a level of the one or more treatment currents responsively to the detected voltage difference.

Inventive concept 23. The system according to any one of inventive concepts 1-8, wherein the control circuitry is configured to apply the one or more treatment currents as direct currents.

Inventive concept 24. The system according to inventive concept 23, wherein the control circuitry is configured to apply the one or more direct currents as a plurality of pulses.

There is further provided, in accordance with an inventive concept 25 of the present application, an electroosmotic Alzheimer's disease-treatment system for treating a subject identified as at risk of or suffering from Alzheimer's disease, the system including:
midplane treatment electrodes, adapted to be disposed over a superior sagittal sinus, outside and in electrical contact with a skull of a head of the subject;
lateral treatment electrodes, adapted to be disposed between 1 and 12 cm of a sagittal midplane of the skull; and
control circuitry, configured to electroosmotically drive fluid from a subarachnoid space to the superior sagittal sinus, by applying one or more treatment currents between (a) one or more of the midplane treatment electrodes and (b) one or more of the lateral treatment electrodes.

Inventive concept 26. The system according to inventive concept 25, wherein the control circuitry is configured to facilitate clearance of amyloid beta from the subarachnoid space to the superior sagittal sinus by electroosmotically driving the fluid from the subarachnoid space to the superior sagittal sinus.

Inventive concept 27. The system according to inventive concept 25, wherein the control circuitry is configured to facilitate clearance of metal ions from the subarachnoid space to the superior sagittal sinus by electroosmotically driving the fluid from the subarachnoid space to the superior sagittal sinus.

Inventive concept 28. The system according to inventive concept 25, wherein the control circuitry is configured to apply the one or more treatment currents with an average amplitude of between 1 and 3 milliamps.

Inventive concept 29. The system according to any one of inventive concepts 25-28, wherein the lateral treatment electrodes are adapted to be disposed outside and in electrical contact with the skull.

Inventive concept 30. The system according to inventive concept 29, wherein the lateral treatment electrodes are adapted to be disposed outside the head.

Inventive concept 31. The system according to inventive concept 30, wherein the lateral treatment electrodes are adapted to be disposed on an external surface of the head.

Inventive concept 32. The system according to inventive concept 29, wherein the lateral treatment electrodes are adapted to be disposed under skin of the head.

Inventive concept 33. The system according to any one of inventive concepts 25-28, wherein the midplane treatment electrodes are adapted to be disposed outside the head.

Inventive concept 34. The system according to inventive concept 33, wherein the midplane treatment electrodes are adapted to be disposed on an external surface of the head.

Inventive concept 35. The system according to any one of inventive concepts 25-28, wherein the midplane treatment electrodes are adapted to be disposed under skin of the head.

Inventive concept 36. The system according to any one of inventive concepts 25-28, wherein the lateral treatment electrodes are adapted to be disposed under an arachnoid mater of the subject.

Inventive concept 37. The system according to inventive concept 36, wherein the lateral treatment electrodes are adapted to be disposed in the subarachnoid space.

Inventive concept 38. The system according to inventive concept 36, wherein the lateral treatment electrodes are adapted to be disposed in gray or white matter of a brain of the subject.

Inventive concept 39. The system according to any one of inventive concepts 25-28,
wherein the system further includes (a) a midplane lead, which is adapted to be disposed outside the skull, and (b) a lateral lead, which is adapted to be disposed within 1 and 12 cm of the sagittal midplane of the skull,
wherein the system includes at least five midplane treatment electrodes that are disposed along the midplane lead, and
wherein the system includes at least five lateral treatment electrodes that are disposed along the lateral lead.

Inventive concept 40. The system according to any one of inventive concepts 25-28, wherein the control circuitry is configured to configure the midplane treatment electrodes as cathodes, and the lateral treatment electrodes as anodes.

Inventive concept 41. The system according to any one of inventive concepts 25-28, wherein the lateral treatment electrodes include:
left lateral treatment electrodes, which are adapted to be disposed left of the sagittal midplane of the skull; and
right lateral treatment electrodes, which are adapted to be disposed right of the sagittal midplane of the skull.

Inventive concept 42. The system according to inventive concept 41, wherein the control circuitry is configured to configure the midplane treatment electrodes as cathodes, and the left and the right lateral treatment electrodes as left and right anodes, respectively.

Inventive concept 43. The system according to inventive concept 41,
wherein the system further includes (a) a midplane lead, which is adapted to be disposed outside the skull, (b) a left lateral lead, which is adapted to be disposed outside the skull, and (c) a right lateral lead, which is adapted to be disposed outside the skull,
wherein the midplane treatment electrodes are disposed along the lead,
wherein the system includes at least five left lateral treatment electrodes that are disposed along the left lateral lead, and
wherein the system includes at least five right lateral treatment electrodes that are disposed along the right lateral lead.

Inventive concept 44. The system according to inventive concept 41, wherein the control circuitry is configured to apply the one or more treatment currents between (a) one or more of the midplane treatment electrodes and (b) one or more of the lateral treatment electrodes includes activating the control circuitry to apply:
a first treatment current between a first one of the midplane treatment electrodes and a first one of the left lateral treatment electrodes, a second treatment current between the first one of the midplane treatment electrodes and a first one of the right lateral treatment electrodes,
a third treatment current between a second one of the midplane treatment electrodes and a second one of the left lateral treatment electrodes, and
a fourth treatment current between the second one of the midplane treatment electrodes and a second one of the right lateral treatment electrodes.

Inventive concept 45. The system according to inventive concept 44, wherein the control circuitry is configured to configure the midplane treatment electrodes as cathodes, and the left and the right lateral treatment electrodes as left and right anodes, respectively.

Inventive concept 46. The system according to any one of inventive concepts 25-28, wherein the control circuitry is configured to:
detect a voltage difference between the subarachnoid space and the superior sagittal sinus, and
set a level of the one or more treatment currents responsively to the detected voltage difference.

Inventive concept 47. The system according to inventive concept 46,
wherein the system further includes a first detection electrode, adapted to be implanted in the subarachnoid space, and a second detection electrode, adapted to be implanted in the superior sagittal sinus, and
wherein the control circuitry is detect the voltage difference between the first and the second detection electrodes.

Inventive concept 48. The system according to inventive concept 46, wherein the control circuitry is configured to detect the voltage difference between at least one of the midplane treatment electrodes and at least one of the lateral treatment electrodes.

Inventive concept 49. The system according to inventive concept 46,
wherein the system further includes a detection electrode, which is configured to be implanted in the superior sagittal sinus, and
wherein the control circuitry is configured to detect the voltage difference between the detection electrode and at least one of the lateral treatment electrodes.

Inventive concept 50. The system according to inventive concept 46,
wherein the system further includes a detection electrode, which is configured to be implanted in the subarachnoid space, and
wherein the control circuitry is configured to detect the voltage difference between the detection electrode and at least one of the midplane treatment electrodes.

Inventive concept 51. The system according to any one of inventive concepts 25-28, wherein the control circuitry is configured to apply the one or more treatment currents as direct currents.

Inventive concept 52. The system according to inventive concept 51, wherein the control circuitry is configured to apply the one or more direct currents as a plurality of pulses.

There is still further provided, in accordance with an inventive concept 53 of the present application, an electroosmotic Alzheimer's disease-treatment system for treating a subject identified as at risk of or suffering from Alzheimer's disease, the system including:
one or more midplane treatment electrodes, adapted to be disposed over a superior sagittal sinus, outside and in electrical contact with a skull of a head of the subject;
one or more lateral treatment electrodes, adapted to be disposed between 1 and 12 cm of a sagittal midplane of the skull; and
control circuitry, configured to electroosmotically drive fluid from a subarachnoid space to the superior sagittal sinus, by applying one or more treatment currents between (a) one or more of the midplane treatment electrodes and (b) one or more of the lateral treatment electrodes.

Inventive concept 54. The system according to inventive concept 53, wherein the one or more lateral treatment electrodes include:
one or more left lateral treatment electrodes, which are adapted to be disposed left of the sagittal midplane of the skull,
one or more right lateral treatment electrodes, which are adapted to be disposed right of the sagittal midplane of the skull.

Inventive concept 55. The system according to inventive concept 54, wherein the control circuitry is configured to configure the one or more midplane treatment electrodes as one or more cathodes, the one or more left lateral treatment electrodes as one or more left anodes, and the one or more right lateral treatment electrodes as one or more right anodes.

Inventive concept 56. The system according to inventive concept 53, wherein the one or more midplane treatment electrodes include an elongate electrode having a length of at least 10 cm.

Inventive concept 57. The system according to inventive concept 53, wherein the one or more lateral treatment electrodes include an elongate electrode having a length of at least 10 cm.

Inventive concept There is additionally provided, in accordance with an inventive concept 58 of the present application, an electrical amyloid beta-clearance system for treating a subject identified as at risk of or suffering from cerebral amyloid angiopathy (CAA), the system including:
midplane treatment electrodes, adapted to be disposed over a superior sagittal sinus, outside and in electrical contact with a skull of a head of the subject;
lateral treatment electrodes, adapted to be disposed between 1 and 12 cm of a sagittal midplane of the skull; and
control circuitry, configured to clear amyloid beta from a subarachnoid space to the superior sagittal sinus, by applying one or more treatment currents between (a) one or more of the midplane treatment electrodes and (b) one or more of the lateral treatment electrodes.

Inventive concept 59. The system according to inventive concept 58, wherein the control circuitry is configured to clear the amyloid beta by electroosmotically (hiving fluid from the subarachnoid space to the superior sagittal sinus.

Inventive concept 60. The system according to inventive concept 59, wherein the control circuitry is configured to configure the midplane treatment electrodes as cathodes, and the lateral treatment electrodes as anodes.

Inventive concept 61. The system according to inventive concept 59,
wherein the lateral treatment electrodes include (a) left lateral treatment electrodes, which are adapted to be disposed left of the sagittal midplane of the skull, and (b) right lateral treatment electrodes, which are adapted to be disposed right of the sagittal midplane of the skull, and
wherein the control circuitry is configured to configure the midplane treatment electrodes as cathodes, and the left and the right lateral treatment electrodes as left and right anodes, respectively.

Inventive concept 62. The system according to inventive concept 58, wherein the control circuitry is configured to clear the amyloid beta by electrophoretically driving the amyloid beta from the subarachnoid space to the superior sagittal sinus.

Inventive concept 63. The system according to inventive concept 62, wherein the control circuitry is configured to configure the midplane treatment electrodes as anodes, and the lateral treatment electrodes as cathodes.

Inventive concept 64. The system according to inventive concept 62, wherein the lateral treatment electrodes include (a) left lateral treatment electrodes, which are adapted to be disposed left of the sagittal midplane of the skull, and (b) right lateral treatment electrodes, which are adapted to be disposed right of the sagittal midplane of the skull, and wherein the control circuitry is configured to configure the midplane treatment electrodes as anodes, and the left and the right lateral treatment electrodes as left and right cathodes, respectively.

Inventive concept 65. The system according to inventive concept 58, wherein the control circuitry is configured to apply the one or more treatment currents with an average amplitude of between 1 and 3 milliamps.

Inventive concept 66. The system according to any one of inventive concepts 58-65, wherein the lateral treatment electrodes are adapted to be disposed outside and in electrical contact with the skull.

Inventive concept 67. The system according to inventive concept 66, wherein the lateral treatment electrodes are adapted to be disposed outside the head.

Inventive concept 68. The system according to inventive concept 67, wherein the lateral treatment electrodes are adapted to be disposed on an external surface of the head.

Inventive concept 69. The system according to inventive concept 66, wherein the lateral treatment electrodes are adapted to be implanted under skin of the head.

Inventive concept 70. The system according to any one of inventive concepts 58-65, wherein the midplane treatment electrodes are adapted to be disposed outside the head.

Inventive concept 71. The system according to inventive concept 70, wherein the midplane treatment electrodes are adapted to be disposed on an external surface of the head.

Inventive concept 72. The system according to any one of inventive concepts 58-65, wherein the midplane treatment electrodes are adapted to be implanted under skin of the head.

Inventive concept 73. The system according to any one of inventive concepts 58-65, wherein the lateral treatment electrodes are adapted to be implanted under an arachnoid mater of the subject.

Inventive concept 74. The system according to inventive concept 73, wherein the lateral treatment electrodes are adapted to be disposed in the subarachnoid space.

Inventive concept 75. The system according to inventive concept 73, wherein the lateral treatment electrodes are adapted to be disposed in gray or white matter of a brain of the subject.

Inventive concept 76. The system according to any one of inventive concepts 58-65, wherein the system further includes (a) a midplane lead, which is adapted to be disposed outside the skull, and (b) a lateral lead, which is adapted to be disposed within 1 and 12 cm of the sagittal midplane of the skull, wherein the system includes at least five midplane treatment electrodes that are disposed along the midplane lead, and wherein the system includes at least five lateral treatment electrodes that are disposed along the lateral lead.

Inventive concept 77. The system according to any one of inventive concepts 58-65, wherein the lateral treatment electrodes include:

left lateral treatment electrodes, which are adapted to be disposed left of the sagittal midplane of the skull; and right lateral treatment electrodes, which are adapted to be disposed right of the sagittal midplane of the skull.

Inventive concept 78. The system according to inventive concept 77, wherein the control circuitry is configured to apply the one or more treatment currents between (a) one or more of the midplane treatment electrodes and (b) one or more of the lateral treatment electrodes includes activating the control circuitry to apply:

a first treatment current between a first one of the midplane treatment electrodes and a first one of the left lateral treatment electrodes, a second treatment current between the first one of the midplane treatment electrodes and a first one of the right lateral treatment electrodes, a third treatment current between a second one of the midplane treatment electrodes and a second one of the left lateral treatment electrodes, and a fourth treatment current between the second one of the midplane treatment electrodes and a second one of the right lateral treatment electrodes.

Inventive concept 79. The system according to any one of inventive concepts 58-65, wherein the control circuitry is configured to:

detect a voltage difference between the subarachnoid space and the superior sagittal sinus, and set a level of the one or more treatment currents responsively to the detected voltage difference.

Inventive concept 80. The system according to any one of inventive concepts 58-65, wherein the control circuitry is configured to apply the one or more treatment currents as direct currents.

Inventive concept 81. The system according to inventive concept 80, wherein the control circuitry is configured to apply the one or more direct currents as a plurality of pulses.

There is yet additionally provided, in accordance with an inventive concept 82 of the present application, an electroosmotic hydrocephalus-treatment system for treating a subject identified as suffering from hydrocephalus, the system including:

midplane treatment electrodes, adapted to be disposed over a superior sagittal sinus, outside and in electrical contact with a skull of a head of the subject;

lateral treatment electrodes, adapted to be disposed between 1 and 12 cm of a sagittal midplane of the skull; and control circuitry, configured to electroosmotically drive fluid from a subarachnoid space to the superior sagittal sinus, by applying one or more treatment currents between (a) one or more of the midplane treatment electrodes and (b) one or more of the lateral treatment electrodes.

Inventive concept 83. The system according to inventive concept 82, wherein the control circuitry is configured to configure the midplane treatment electrodes as cathodes, and the lateral treatment electrodes as anodes.

Inventive concept 84. The system according to inventive concept 82, wherein the control circuitry is configured to apply the one or more treatment currents with an average amplitude of between 1 and 3 milliamps.

Inventive concept 85. The system according to any one of inventive concepts 82-84, wherein the lateral treatment electrodes are adapted to be disposed outside and in electrical contact with the skull.

Inventive concept 86. The system according to inventive concept 85, wherein the lateral treatment electrodes are adapted to be disposed outside the head.

Inventive concept 87. The system according to inventive concept 86, wherein the lateral treatment electrodes are adapted to be disposed on an external surface of the head.

Inventive concept 88. The system according to inventive concept 85, wherein the lateral treatment electrodes are adapted to be disposed under skin of the head.

Inventive concept 89. The system according to any one of inventive concepts 82-84, wherein the midplane treatment electrodes are adapted to be disposed outside the head.

Inventive concept 90. The system according to inventive concept 89, wherein the midplane treatment electrodes are adapted to be disposed on an external surface of the head.

Inventive concept 91. The system according to any one of inventive concepts 82-84, wherein the midplane treatment electrodes are adapted to be disposed under skin of the head.

Inventive concept 92. The system according to any one of inventive concepts 82-84, wherein the lateral treatment electrodes are adapted to be disposed under an arachnoid mater of the subject.

Inventive concept 93. The system according to inventive concept 92, wherein the lateral treatment electrodes are adapted to be disposed in the subarachnoid space.

Inventive concept 94. The system according to inventive concept 92, wherein the lateral treatment electrodes are adapted to be disposed in gray or white matter of a brain of the subject.

Inventive concept 95. The system according to any one of inventive concepts 82-84,
wherein the system further includes (a) a midplane lead, which is adapted to be disposed outside the skull, and (b) a lateral lead, which is adapted to be disposed within 1 and 12 cm of the sagittal midplane of the skull,
wherein the system includes at least five midplane treatment electrodes that are disposed along the midplane lead, and
wherein the system includes at least five lateral treatment electrodes that are disposed along the lateral lead.

Inventive concept 96. The system according to any one of inventive concepts 82-84, wherein the lateral treatment electrodes include:
left lateral treatment electrodes, which are adapted to be disposed left of the sagittal midplane of the skull; and
right lateral treatment electrodes, which are adapted to be disposed right of the sagittal midplane of the skull.

Inventive concept 97. The system according to inventive concept 96, wherein the control circuitry is configured to configure the midplane treatment electrodes as cathodes, and the left and the right lateral treatment electrodes as left and right anodes, respectively.

Inventive concept 98. The system according to inventive concept 96,
wherein the system further includes (a) a midplane lead, which is adapted to be disposed outside the skull, (b) a left lateral lead, which is adapted to be disposed outside the skull, and (c) a right lateral lead, which is adapted to be disposed outside the skull,
wherein the midplane treatment electrodes are disposed along the lead,
wherein the system includes at least five left lateral treatment electrodes that are disposed along the left lateral lead, and
wherein the system includes at least five right lateral treatment electrodes that are disposed along the right lateral lead.

Inventive concept 99. The system according to inventive concept 96, wherein the control circuitry is configured to apply the one or more treatment currents between (a) one or more of the midplane treatment electrodes and (b) one or more of the lateral treatment electrodes includes activating the control circuitry to apply:
a first treatment current between a first one of the midplane treatment electrodes and a first one of the left lateral treatment electrodes,
a second treatment current between the first one of the midplane treatment electrodes and a first one of the right lateral treatment electrodes,
a third treatment current between a second one of the midplane treatment electrodes and a second one of the left lateral treatment electrodes, and
a fourth treatment current between the second one of the midplane treatment electrodes and a second one of the right lateral treatment electrodes.

Inventive concept 100. The system according to inventive concept 99, wherein the control circuitry is configured to configure the midplane treatment electrodes as cathodes, and the left and the right lateral treatment electrodes as left and right anodes, respectively.

Inventive concept 101. The system according to any one of inventive concepts 82-84, wherein the control circuitry is configured to:
detect a voltage difference between the subarachnoid space and the superior sagittal sinus, and
set a level of the one or more treatment currents responsively to the detected voltage difference.

Inventive concept 102. The system according to inventive concept 101,
wherein the system further includes a first detection electrode, adapted to be implanted in the subarachnoid space, and a second detection electrode, adapted to be implanted in the superior sagittal sinus, and
wherein the control circuitry is detect the voltage difference between the first and the second detection electrodes.

Inventive concept 103. The system according to inventive concept 101, wherein the control circuitry is configured to detect the voltage difference between at least one of the midplane treatment electrodes and at least one of the lateral treatment electrodes.

Inventive concept 104. The system according to inventive concept 101,
wherein the system further includes a detection electrode, which is configured to be implanted in the superior sagittal sinus, and
wherein the control circuitry is configured to detect the voltage difference between the detection electrode and at least one of the lateral treatment electrodes.

Inventive concept 105. The system according to inventive concept 101,
wherein the system further includes a detection electrode, which is configured to be implanted in the subarachnoid space, and
wherein the control circuitry is configured to detect the voltage difference between the detection electrode and at least one of the midplane treatment electrodes.

Inventive concept 106. The system according to any one of inventive concepts 82-84, wherein the control circuitry is configured to apply the one or more treatment currents as direct currents.

Inventive concept 107. The system according to inventive concept 106, wherein the control circuitry is configured to apply the one or more direct currents as a plurality of pulses.

There is also provided, in accordance with an inventive concept 108 of the present application, apparatus for treating a subject identified as at risk of or suffering from Alzheimer's disease, the apparatus including:

exactly three leads, consisting of a midplane lead, a left lateral lead, and a right lateral lead;

at least five midplane electrodes, which are disposed along the midplane lead at an average distance of at least 1 cm between longitudinally-adjacent pairs of the midplane electrodes, measured between longitudinal midpoints of the midplane electrodes;

at least five left lateral electrodes, which are disposed along the left lateral lead at an average distance of at least 1 cm between longitudinally-adjacent pairs of the left lateral electrodes, measured between longitudinal midpoints of the left lateral electrodes;

at least five right lateral electrodes, which are disposed along the right lateral lead at an average distance of at least 1 cm between longitudinally-adjacent pairs of the right lateral electrodes, measured between longitudinal midpoints of the right lateral electrodes; and a housing, which includes control circuitry, to which the midplane, the left lateral, and the right lateral electrodes are electrically coupled via the midplane lead, the left lateral lead, and the right lateral lead, respectively, the control circuitry configured to:

configure the midplane treatment electrodes as cathodes, and the left and the right lateral treatment electrodes as left and right anodes, respectively, apply respective treatment currents between (a) (i) one or more of the midplane treatment electrodes and (ii) one or more of the left lateral treatment electrodes, and (b) (i) one or more of the midplane treatment electrodes and (ii) one or more of the right lateral treatment electrodes, and configure the treatment currents to treat the subject by electroosmotically driving fluid from a subarachnoid space to a superior sagittal sinus of the subject.

Inventive concept 109. The apparatus according to inventive concept 108, wherein the control circuitry is configured to apply the treatment currents with an average amplitude of between 1 and 3 milliamps.

Inventive concept 110. The apparatus according to inventive concept 108, wherein the housing is configured to be implanted under skin of the subject.

Inventive concept 111. The apparatus according to inventive concept 108, wherein the control circuitry is configured to apply:

a first treatment current between a first one of the midplane treatment electrodes and a first one of the left lateral treatment electrodes, a second treatment current between the first one of the midplane treatment electrodes and a first one of the right lateral treatment electrodes, a third treatment current between a second one of the midplane treatment electrodes and a second one of the left lateral treatment electrodes, and a fourth treatment current between the second one of the midplane treatment electrodes and a second one of the right lateral treatment electrodes.

Inventive concept 112. The apparatus according to inventive concept 108, wherein the control circuitry is configured to:

detect a voltage difference between the subarachnoid space and the superior sagittal sinus; and set a level of the treatment currents responsively to the detected voltage difference.

Inventive concept 113. The apparatus according to inventive concept 108, wherein the control circuitry is configured to apply the treatment currents as direct current.

Inventive concept 114. The apparatus according to inventive concept 113, wherein the control circuitry is configured to apply the direct currents as a plurality of pulses.

There is further provided, in accordance with an inventive concept 115 of the present application, a method including:

disposing midplane treatment electrodes over a superior sagittal sinus, outside and in electrical contact with a skull of a head of a subject identified as at risk of or suffering from Alzheimer's disease;

disposing lateral treatment electrodes between 1 and 12 cm of a sagittal midplane: of the skull; and treating the subject by clearing amyloid beta from a subarachnoid space to the superior sagittal sinus, by activating control circuitry to apply one or more treatment currents between (a) one or more of the midplane treatment electrodes and (b) one or more of the lateral treatment electrodes.

Inventive concept 116. The method according to inventive concept 115, wherein clearing the amyloid beta includes electroosmotically (hiving fluid from the subarachnoid space to the superior sagittal sinus.

Inventive concept 117. The method according to inventive concept 116, wherein activating the control circuitry includes activating the control circuitry to configure the midplane treatment electrodes as cathodes, and the lateral treatment electrodes as anodes.

Inventive concept 118. The method according to inventive concept 116, wherein the lateral treatment electrodes include left lateral treatment electrodes and right lateral treatment electrodes, wherein disposing the lateral treatment electrodes includes disposing the left lateral treatment electrodes left of the sagittal midplane of the skull, and disposing the right lateral treatment electrodes right of the sagittal midplane of the skull, and wherein activating the control circuitry includes activating the control circuitry to configure the midplane treatment electrodes as cathodes, and the left and the right lateral treatment electrodes as left and right anodes, respectively.

Inventive concept 119. The method according to inventive concept 116, wherein electroosmotically driving the fluid includes:

detecting, by the control circuitry, a voltage difference between the subarachnoid space and the superior sagittal sinus; and setting, by the control circuitry, a level of the one or more treatment currents responsively to the detected voltage difference.

Inventive concept 120. The method according to inventive concept 115, wherein clearing the amyloid beta includes electrophoretically driving the amyloid beta from the subarachnoid space to the superior sagittal sinus.

Inventive concept 121. The method according to inventive concept 120, wherein activating the control circuitry includes activating the control circuitry to configure the midplane treatment electrodes as anodes, and the lateral treatment electrodes as cathodes.

Inventive concept 122. The method according to inventive concept 120, wherein the lateral treatment electrodes include left lateral treatment electrodes and right lateral treatment electrodes, wherein disposing the lateral treatment electrodes includes disposing the left lateral treatment electrodes left of the sagittal midplane of the skull, and disposing the right lateral treatment electrodes right of the sagittal midplane of the skull, and wherein activating the control circuitry includes activating the control circuitry to configure the midplane treatment electrodes as anodes, and the left and the right lateral treatment electrodes as left and right cathodes, respectively.

Inventive concept 123. The method according to inventive concept 115, wherein activating the control circuitry includes activating the control circuitry to apply the one or more treatment currents with an average amplitude of between 1 and 3 milliamps.

Inventive concept 124. The method according to inventive concept 115, wherein disposing the lateral treatment electrodes includes disposing the lateral treatment electrodes outside and in electrical contact with the skull.

Inventive concept 125. The method according to inventive concept 124, wherein disposing the lateral treatment electrodes includes disposing the lateral treatment electrodes between 4 and 12 cm of the sagittal midplane of the skull.

Inventive concept 126. The method according to inventive concept 124, wherein disposing the lateral treatment electrodes includes disposing the lateral treatment electrodes outside the head.

Inventive concept 127. The method according to inventive concept 126, wherein disposing the lateral treatment electrodes includes disposing the lateral treatment electrodes on an external surface of the head.

Inventive concept 128. The method according to inventive concept 124, wherein disposing the lateral treatment electrodes includes implanting the lateral treatment electrodes under skin of the head.

Inventive concept 129. The method according to inventive concept 115, wherein disposing the midplane treatment electrodes includes disposing the midplane treatment electrodes outside the head.

Inventive concept 130. The method according to inventive concept 129, wherein disposing the midplane treatment electrodes includes disposing the midplane treatment electrodes on an external surface of the head.

Inventive concept 131. The method according to inventive concept 115, wherein disposing the midplane treatment electrodes includes implanting the midplane treatment electrodes under skin of the head.

Inventive concept 132. The method according to inventive concept 115, wherein disposing the lateral treatment electrodes includes implanting the lateral treatment electrodes under an arachnoid mater of the subject.

Inventive concept 133. The method according to inventive concept 132, wherein disposing the lateral treatment electrodes includes disposing the lateral treatment electrodes between 1 and 3 cm of the sagittal midplane of the skull.

Inventive concept 134. The method according to inventive concept 132, wherein disposing the lateral treatment electrodes includes disposing the lateral treatment electrodes in the subarachnoid space.

Inventive concept 135. The method according to inventive concept 132, wherein disposing the lateral treatment electrodes includes disposing the lateral treatment electrodes in gray or white matter of a brain of the subject.

Inventive concept 136. The method according to inventive concept 115, wherein disposing the midplane treatment electrodes includes disposing the midplane treatment electrodes within 10 mm of the sagittal midplane of the skull.

Inventive concept 137. The method according to inventive concept 115, wherein disposing the midplane treatment electrodes includes disposing at least five midplane treatment electrodes over the superior sagittal sinus.

Inventive concept 138. The method according to inventive concept 137, wherein disposing the lateral treatment electrodes includes disposing at least five lateral treatment electrodes between 1 and 12 cm of the sagittal midplane of the skull.

Inventive concept 139. The method according to inventive concept 138, wherein disposing the midplane treatment electrodes includes disposing a midplane lead outside the skull, and wherein the midplane treatment electrodes are disposed along the midplane lead, and wherein disposing the lateral treatment electrodes includes disposing a lateral lead within 1 and 12 cm of the sagittal midplane of the skull, and wherein the lateral treatment electrodes are disposed along the lateral lead.

Inventive concept 140. The method according to inventive concept 115, wherein the lateral treatment electrodes include left lateral treatment electrodes and right lateral treatment electrodes, and wherein disposing the lateral treatment electrodes includes disposing the left lateral treatment electrodes left of the sagittal midplane of the skull, and disposing the right lateral treatment electrodes right of the sagittal midplane of the skull.

Inventive concept 141. The method according to inventive concept 140, wherein disposing the left lateral treatment electrodes includes disposing the left lateral treatment electrodes such that at least one of the left lateral treatment electrodes is at least 1 cm from another one of the left lateral treatment electrodes, and wherein disposing the right lateral treatment electrodes includes disposing the right lateral treatment electrodes such that at least one of the right lateral treatment electrodes is at least 1 cm from another one of the right lateral treatment electrodes.

Inventive concept 142. The method according to inventive concept 140, wherein activating the control circuitry to apply the one or more treatment currents between (a) one or more of the midplane treatment electrodes and (b) one or more of the lateral treatment electrodes includes activating the control circuitry to apply:

a first treatment current between a first one of the midplane treatment electrodes and a first one of the left lateral treatment electrodes, a second treatment current between the first one of the midplane treatment electrodes and a first one of the right lateral treatment electrodes, a third treatment current between a second one of the midplane treatment electrodes and a second one of the left lateral treatment electrodes, and a fourth treatment current between the second one of the midplane treatment electrodes and a second one of the right lateral treatment electrodes.

Inventive concept 143. The method according to inventive concept 115, wherein activating the control circuitry includes activating the control circuitry to apply the one or more treatment currents as direct currents.

Inventive concept 144. The method according to inventive concept 143, wherein activating the control circuitry includes activating the control circuitry to apply the one or more direct currents as a plurality of pulses.

There is still further provided, in accordance with an inventive concept 145 of the present application, a method including:

disposing midplane treatment electrodes over a superior sagittal sinus, outside and in electrical contact with a skull of a head of a subject identified as at risk of or suffering from Alzheimer's disease;

disposing lateral treatment electrodes between 1 and 12 cm of a sagittal midplane of the skull; and treating the subject by electroosmotically driving fluid from a subarachnoid space to the superior sagittal sinus, by activating control circuitry to apply one or more treatment currents between (a) one or more of the midplane treatment electrodes and (b) one or more of the lateral treatment electrodes.

Inventive concept 146. The method according to inventive concept 145, wherein treating the subject includes facilitating clearance of amyloid beta from the subarachnoid space to the superior sagittal sinus by electroosmotically driving the fluid from the subarachnoid space to the superior sagittal sinus.

Inventive concept 147. The method according to inventive concept 145, wherein treating the subject includes facilitating clearance of metal ions from the subarachnoid space to the superior sagittal sinus by electroosmotically driving the fluid from the subarachnoid space to the superior sagittal sinus.

Inventive concept 148. The method according to inventive concept 145, wherein activating the control circuitry includes activating the control circuitry to apply the one or more treatment currents with an average amplitude of between 1 and 3 milliamps.

Inventive concept 149. The method according to inventive concept 145, wherein disposing the lateral treatment electrodes includes disposing the lateral treatment electrodes outside and in electrical contact with the skull.

Inventive concept 150. The method according to inventive concept 149, wherein disposing the lateral treatment electrodes includes disposing the lateral treatment electrodes between 4 and 12 cm of the sagittal midplane of the skull.

Inventive concept 151. The method according to inventive concept 149, wherein disposing the midplane and the lateral treatment electrodes includes disposing each of the lateral treatment electrodes between 1 and 12 cm of at least one of the midplane treatment electrodes.

Inventive concept 152. The method according to inventive concept 149, wherein disposing the midplane and the lateral treatment electrodes includes disposing each of the lateral treatment electrodes between 1 and 12 cm of one of the midplane treatment electrodes that is closest to the lateral treatment electrode.

Inventive concept 153. The method according to inventive concept 149, wherein disposing the lateral treatment electrodes includes disposing the lateral treatment electrodes outside the head.

Inventive concept 154. The method according to inventive concept 153, wherein disposing the lateral treatment electrodes includes disposing the lateral treatment electrodes on an external surface of the head.

Inventive concept 155. The method according to inventive concept 149, wherein disposing the lateral treatment electrodes includes implanting the lateral treatment electrodes under skin of the head.

Inventive concept 156. The method according to inventive concept 145, wherein disposing the midplane treatment electrodes includes disposing the midplane treatment electrodes outside the head.

Inventive concept 157. The method according to inventive concept 156, wherein disposing the midplane treatment electrodes includes disposing the midplane treatment electrodes on an external surface of the head.

Inventive concept 158. The method according to inventive concept 145, wherein disposing the midplane treatment electrodes includes implanting the midplane treatment electrodes under skin of the head.

Inventive concept 159. The method according to inventive concept 145, wherein disposing the lateral treatment electrodes includes implanting the lateral treatment electrodes under an arachnoid mater of the subject.

Inventive concept 160. The method according to inventive concept 159, wherein disposing the lateral treatment electrodes includes disposing the lateral treatment electrodes between 1 and 3 cm of the sagittal midplane of the skull.

Inventive concept 161. The method according to inventive concept 159, wherein disposing the midplane and the lateral treatment electrodes includes disposing each of the lateral treatment electrodes between 1 and 3 cm of at least one of the midplane treatment electrodes.

Inventive concept 162. The method according to inventive concept 159, wherein disposing the midplane and the lateral treatment electrodes includes disposing each of the lateral treatment electrodes between 1 and 3 cm of one of the midplane treatment electrodes that is closest to the lateral treatment electrode.

Inventive concept 163. The method according to inventive concept 159, wherein disposing the lateral treatment electrodes includes disposing the lateral treatment electrodes in the subarachnoid space.

Inventive concept 164. The method according to inventive concept 159, wherein disposing the lateral treatment electrodes includes disposing the lateral treatment electrodes in gray or white matter of a brain of the subject.

Inventive concept 165. The method according to inventive concept 145, wherein disposing the midplane treatment electrodes includes disposing the midplane treatment electrodes within 10 mm of the sagittal midplane of the skull.

Inventive concept 166. The method according to inventive concept 145, further including implanting the control circuitry under skin of the subject.

Inventive concept 167. The method according to inventive concept 145, wherein disposing the midplane treatment electrodes includes disposing the midplane treatment electrodes such that at least one of the midplane treatment electrodes is at least 5 mm from another one of the midplane treatment electrodes.

Inventive concept 168. The method according to inventive concept 145, wherein disposing the lateral treatment electrodes includes disposing the lateral treatment electrodes such that at least one of the lateral treatment electrodes is at least 5 mm from another one of the lateral treatment electrodes.

Inventive concept 169. The method according to inventive concept 145, wherein disposing the midplane treatment electrodes includes disposing at least five midplane treatment electrodes over the superior sagittal sinus.

Inventive concept 170. The method according to inventive concept 169, wherein disposing the lateral treatment electrodes includes disposing at least five lateral treatment electrodes between 1 and 12 cm of the sagittal midplane of the skull.

Inventive concept 171. The method according to inventive concept 170, wherein disposing the midplane treatment electrodes includes disposing a midplane lead outside the skull, and wherein the midplane treatment electrodes are disposed along the midplane lead, and wherein disposing the lateral treatment electrodes includes disposing a lateral lead within 1 and 12 cm of the sagittal midplane of the skull, and wherein the lateral treatment electrodes are disposed along the lateral lead.

Inventive concept 172. The method according to inventive concept 145, wherein activating the control circuitry includes activating the control circuitry to configure the midplane treatment electrodes as cathodes, and the lateral treatment electrodes as anodes.

Inventive concept 173. The method according to inventive concept 145, wherein the lateral treatment electrodes include left lateral treatment electrodes and right lateral treatment electrodes, and wherein disposing the lateral treatment electrodes includes disposing the left lateral treatment electrodes left of the sagittal midplane of the skull, and disposing the right lateral treatment electrodes right of the sagittal midplane of the skull.

Inventive concept 174. The method according to inventive concept 173, wherein activating the control circuitry includes activating the control circuitry to configure the midplane treatment electrodes as cathodes, and the left and the right lateral treatment electrodes as left and right anodes, respectively.

Inventive concept 175. The method according to inventive concept 173, wherein disposing the left lateral treatment electrodes includes disposing the left lateral treatment electrodes such that at least one of the left lateral treatment electrodes is at least 1 cm from another one of the left lateral treatment electrodes, and wherein disposing the right lateral treatment electrodes includes disposing the right lateral treatment electrodes such that at least one of the right lateral treatment electrodes is at least 1 cm from another one of the right lateral treatment electrodes.

Inventive concept 176. The method according to inventive concept 173, wherein disposing the left lateral treatment electrodes includes disposing at least five left lateral treatment electrodes left of the sagittal midplane of the skull, and wherein disposing the right lateral treatment electrodes includes disposing at least five right lateral treatment electrodes right of the sagittal midplane of the skull.

Inventive concept 177. The method according to inventive concept 176, wherein disposing the midplane treatment electrodes includes disposing a midplane lead outside the skull, and wherein the midplane treatment electrodes are disposed along the lead, wherein disposing the left lateral treatment electrodes includes disposing a left lateral lead outside the skull, and wherein the left lateral treatment electrodes are disposed along the left lateral lead, and wherein disposing the right lateral treatment electrodes includes disposing a right lateral lead outside the skull, and wherein the right lateral treatment electrodes are disposed along the right lateral lead.

Inventive concept 178. The method according to inventive concept 173, wherein activating the control circuitry to apply the one or more treatment currents between (a) one or more of the midplane treatment electrodes and (b) one or more of the lateral treatment electrodes includes activating the control circuitry to apply:

a first treatment current between a first one of the midplane treatment electrodes and a first one of the left lateral treatment electrodes, a second treatment current between the first one of the midplane treatment electrodes and a first one of the right lateral treatment electrodes, a third treatment current between a second one of the midplane treatment electrodes and a second one of the left lateral treatment electrodes, and a fourth treatment current between the second one of the midplane treatment electrodes and a second one of the right lateral treatment electrodes.

Inventive concept 179. The method according to inventive concept 178, wherein activating the control circuitry includes activating the control circuitry to configure the midplane treatment electrodes as cathodes, and the left and the right lateral treatment electrodes as left and right anodes, respectively.

Inventive concept 180. The method according to inventive concept 145, wherein electroosmotically driving the fluid includes:

detecting, by the control circuitry, a voltage difference between the subarachnoid space and the superior sagittal sinus; and setting, by the control circuitry, a level of the one or more treatment currents responsively to the detected voltage difference.

Inventive concept 181. The method according to inventive concept 180, wherein the method further includes implanting a first detection electrode in the subarachnoid space, and a second detection electrode in the superior sagittal sinus, and wherein detecting the voltage difference includes detecting, by the control circuitry, the voltage difference between the first and the second detection electrodes.

Inventive concept 182. The method according to inventive concept 180, wherein detecting the voltage difference includes detecting, by the control circuitry, the voltage difference between at least one of the midplane treatment electrodes and at least one of the lateral treatment electrodes.

Inventive concept 183. The method according to inventive concept 180, wherein the method further includes implanting a detection electrode in the superior sagittal sinus, and wherein detecting the voltage difference includes detecting, by the control circuitry, the voltage difference between the detection electrode and at least one of the lateral treatment electrodes.

Inventive concept 184. The method according to inventive concept 180, wherein the method further includes implanting a detection electrode in the subarachnoid space, and wherein detecting the voltage difference includes detecting, by the control circuitry, the voltage difference between the detection electrode and at least one of the midplane treatment electrodes.

Inventive concept 185. The method according to inventive concept 145, wherein activating the control circuitry includes activating the control circuitry to apply the one or more treatment currents as direct currents.

Inventive concept 186. The method according to inventive concept 185, wherein activating the control circuitry includes activating the control circuitry to apply the one or more direct currents as a plurality of pulses.

There is additionally provided, in accordance with an inventive concept 187 of the present application, a method including:

disposing one or more midplane treatment electrodes over a superior sagittal sinus, outside and in electrical contact with a skull of a head of a subject identified as at risk of or suffering from Alzheimer's disease;

disposing one or more lateral treatment electrodes between 1 and 12 cm of a sagittal midplane of the skull; and treating the subject by electroosmotically driving fluid from a subarachnoid space to the superior sagittal sinus, by activating control circuitry to apply one or more treatment currents between (a) one or more of the midplane treatment electrodes and (b) one or more of the lateral treatment electrodes.

Inventive concept 188. The method according to inventive concept 187, wherein the one or more lateral treatment electrodes include one or more left lateral treatment electrodes and one or more right lateral treatment electrodes, and wherein disposing the one or more lateral treatment electrodes includes disposing the one or more left lateral treatment electrodes left of the sagittal midplane of the skull, and disposing the one or more right lateral treatment electrodes right of the sagittal midplane of the skull.

Inventive concept 189. The method according to inventive concept 188, wherein activating the control circuitry includes activating the control circuitry to configure the one or more midplane treatment electrodes as one or more cathodes, the one or more left lateral treatment electrodes as one or more left anodes, and the one or more right lateral treatment electrodes as one or more right anodes.

Inventive concept 190. The method according to inventive concept 187, wherein the one or more midplane treatment electrodes include an elongate electrode having a length of at least 10 cm.

Inventive concept 191. The method according to inventive concept 187, wherein the one or more lateral treatment electrodes include an elongate electrode having a length of at least 10 cm.

There is yet additionally provided, in accordance with an inventive concept 192 of the present application, a method including:

disposing midplane treatment electrodes over a superior sagittal sinus, outside and in electrical contact with a skull of a head of a subject identified as at risk of or suffering from cerebral amyloid angiopathy (CAA);

disposing lateral treatment electrodes between 1 and 12 cm of a sagittal midplane of the skull; and treating the subject by clearing amyloid beta from a subarachnoid space to the superior sagittal sinus, by activating control circuitry to apply one or more treatment currents between (a) one or more of the midplane treatment electrodes and (b) one or more of the lateral treatment electrodes.

Inventive concept 193. The method according to inventive concept 192, wherein clearing the amyloid beta includes electroosmotically driving fluid from the subarachnoid space to the superior sagittal sinus.

Inventive concept 194. The method according to inventive concept 193, wherein activating the control circuitry includes activating the control circuitry to configure the midplane treatment electrodes as cathodes, and the lateral treatment electrodes as anodes.

Inventive concept 195. The method according to inventive concept 193, wherein the lateral treatment electrodes include left lateral treatment electrodes and right lateral treatment electrodes, wherein disposing the lateral treatment electrodes includes disposing the left lateral treatment electrodes left of the sagittal midplane of the skull, and disposing the right lateral treatment electrodes right of the sagittal midplane of the skull, and wherein activating the control circuitry includes activating the control circuitry to configure the midplane treatment electrodes as cathodes, and the left and the right lateral treatment electrodes as left and right anodes, respectively.

Inventive concept 196. The method according to inventive concept 193, wherein electroosmotically driving the fluid includes:

detecting, by the control circuitry, a voltage difference between the subarachnoid space and the superior sagittal sinus; and setting, by the control circuitry, a level of the one or more treatment currents responsively to the detected voltage difference.

Inventive concept 197. The method according to inventive concept 192, wherein clearing the amyloid beta includes electrophoretically driving the amyloid beta from the subarachnoid space to the superior sagittal sinus.

Inventive concept 198. The method according to inventive concept 197, wherein activating the control circuitry includes activating the control circuitry to configure the midplane treatment electrodes as anodes, and the lateral treatment electrodes as cathodes.

Inventive concept 199. The method according to inventive concept 197, wherein the lateral treatment electrodes include left lateral treatment electrodes and right lateral treatment electrodes, wherein disposing the lateral treatment electrodes includes disposing the left lateral treatment electrodes left of the sagittal midplane of the skull, and disposing the right lateral treatment electrodes right of the sagittal midplane of the skull, and wherein activating the control circuitry includes activating the control circuitry to configure the midplane treatment electrodes as anodes, and the left and the right lateral treatment electrodes as left and right cathodes, respectively.

Inventive concept 200. The method according to inventive concept 192, wherein activating the control circuitry includes activating the control circuitry to apply the one or more treatment currents with an average amplitude of between 1 and 3 milliamps.

Inventive concept 201. The method according to inventive concept 192, wherein disposing the lateral treatment electrodes includes disposing the lateral treatment electrodes outside and in electrical contact with the skull.

Inventive concept 202. The method according to inventive concept 201, wherein disposing the lateral treatment electrodes includes disposing the lateral treatment electrodes between 4 and 12 cm of the sagittal midplane of the skull.

Inventive concept 203. The method according to inventive concept 201, wherein disposing the lateral treatment electrodes includes disposing the lateral treatment electrodes outside the head.

Inventive concept 204. The method according to inventive concept 203, wherein disposing the lateral treatment electrodes includes disposing the lateral treatment electrodes on an external surface of the head.

Inventive concept 205. The method according to inventive concept 201, wherein disposing the lateral treatment electrodes includes implanting the lateral treatment electrodes under skin of the head.

Inventive concept 206. The method according to inventive concept 192, wherein disposing the midplane treatment electrodes includes disposing the midplane treatment electrodes outside the head.

Inventive concept 207. The method according to inventive concept 206, wherein disposing the midplane treatment electrodes includes disposing the midplane treatment electrodes on an external surface of the head.

Inventive concept 208. The method according to inventive concept 192, wherein disposing the midplane treatment electrodes includes implanting the midplane treatment electrodes under skin of the head.

Inventive concept 209. The method according to inventive concept 192, wherein disposing the lateral treatment electrodes includes implanting the lateral treatment electrodes under an arachnoid mater of the subject.

Inventive concept 210. The method according to inventive concept 209, wherein disposing the lateral treatment electrodes includes disposing the lateral treatment electrodes between 1 and 3 cm of the sagittal midplane of the skull.

Inventive concept 211. The method according to inventive concept 209, wherein disposing the lateral treatment electrodes includes disposing the lateral treatment electrodes in the subarachnoid space.

Inventive concept 212. The method according to inventive concept 209, wherein disposing the lateral treatment electrodes includes disposing the lateral treatment electrodes in gray or white matter of a brain of the subject.

Inventive concept 213. The method according to inventive concept 192, wherein disposing the midplane treatment electrodes includes disposing the midplane treatment electrodes within 10 mm of the sagittal midplane of the skull.

Inventive concept 214. The method according to inventive concept 192, wherein disposing the midplane treatment electrodes includes disposing at least five midplane treatment electrodes over the superior sagittal sinus.

Inventive concept 215. The method according to inventive concept 214, wherein disposing the lateral treatment electrodes includes disposing at least five lateral treatment electrodes between 1 and 12 cm of the sagittal midplane of the skull.

Inventive concept 216. The method according to inventive concept 215, wherein disposing the midplane treatment electrodes includes disposing a midplane lead outside the skull, and wherein the midplane treatment electrodes are disposed along the midplane lead, and wherein disposing the lateral treatment electrodes includes disposing a lateral lead within 1 and 12 cm of the sagittal midplane of the skull, and wherein the lateral treatment electrodes are disposed along the lateral lead.

Inventive concept 217. The method according to inventive concept 192, wherein the lateral treatment electrodes include left lateral treatment electrodes and right lateral treatment electrodes, and wherein disposing the lateral treatment electrodes includes disposing the left lateral treatment electrodes left of the sagittal midplane of the skull, and disposing the right lateral treatment electrodes right of the sagittal midplane of the skull.

Inventive concept 218. The method according to inventive concept 217, wherein disposing the left lateral treatment electrodes includes disposing the left lateral treatment electrodes such that at least one of the left lateral treatment electrodes is at least 1 cm from another one of the left lateral treatment electrodes, and wherein disposing the right lateral treatment electrodes includes disposing the right lateral treatment electrodes such that at least one of the right lateral treatment electrodes is at least 1 cm from another one of the right lateral treatment electrodes.

Inventive concept 219. The method according to inventive concept 217, wherein activating the control circuitry to apply the one or more treatment currents between (a) one or more of the midplane treatment electrodes and (b) one or more of the lateral treatment electrodes includes activating the control circuitry to apply:

a first treatment current between a first one of the midplane treatment electrodes and a first one of the left lateral treatment electrodes, a second treatment current between the first one of the midplane treatment electrodes and a first one of the right lateral treatment electrodes, a third treatment current between a second one of the midplane treatment electrodes and a second one of the left lateral treatment electrodes, and a fourth treatment current between the second one of the midplane treatment electrodes and a second one of the right lateral treatment electrodes.

Inventive concept 220. The method according to inventive concept 192, wherein activating the control circuitry includes activating the control circuitry to apply the one or more treatment currents as direct currents.

Inventive concept 221. The method according to inventive concept 220, wherein activating the control circuitry includes activating the control circuitry to apply the one or more direct currents as a plurality of pulses.

There is also provided, in accordance with an inventive concept 222 of the present application, a method including:

disposing midplane treatment electrodes over a superior sagittal sinus, outside and in electrical contact with a skull of a head of a subject identified as suffering from hydrocephalus;

disposing lateral treatment electrodes between 1 and 12 cm of a sagittal midplane of the skull; and treating the subject by electroosmotically driving fluid from a subarachnoid space to the superior sagittal sinus, by activating control circuitry to apply one or more treatment currents between (a) one or more of the midplane treatment electrodes and (b) one or more of the lateral treatment electrodes.

Inventive concept 223. The method according to inventive concept 222, wherein activating the control circuitry includes activating the control circuitry to configure the midplane treatment electrodes as cathodes, and the lateral treatment electrodes as anodes.

Inventive concept 224. The method according to inventive concept 222, wherein the lateral treatment electrodes include left lateral treatment electrodes and right lateral treatment electrodes, wherein disposing the lateral treatment electrodes includes disposing the left lateral treatment electrodes left of the sagittal midplane of the skull, and disposing the right lateral treatment electrodes right of the sagittal midplane of the skull, and wherein activating the control circuitry includes activating the control circuitry to configure the midplane treatment electrodes as cathodes, and the left and the right lateral treatment electrodes as left and right anodes, respectively.

Inventive concept 225. The method according to inventive concept 222, wherein activating the control circuitry includes activating the control circuitry to apply the one or more treatment currents with an average amplitude of between 1 and 3 milliamps.

Inventive concept 226. The method according to inventive concept 222, wherein disposing the lateral treatment electrodes includes disposing the lateral treatment electrodes outside and in electrical contact with the skull.

Inventive concept 227. The method according to inventive concept 226, wherein disposing the lateral treatment electrodes includes disposing the lateral treatment electrodes between 4 and 12 cm of the sagittal midplane of the skull.

Inventive concept 228. The method according to inventive concept 226, wherein disposing the lateral treatment electrodes includes disposing the lateral treatment electrodes outside the head.

Inventive concept 229. The method according to inventive concept 228, wherein disposing the lateral treatment electrodes includes disposing the lateral treatment electrodes on an external surface of the head.

Inventive concept 230. The method according to inventive concept 226, wherein disposing the lateral treatment electrodes includes implanting the lateral treatment electrodes under skin of the head.

Inventive concept 231. The method according to inventive concept 222, wherein disposing the midplane treatment electrodes includes disposing the midplane treatment electrodes outside the head.

Inventive concept 232. The method according to inventive concept 231, wherein disposing the midplane treatment electrodes includes disposing the midplane treatment electrodes on an external surface of the head.

Inventive concept 233. The method according to inventive concept 222, wherein disposing the midplane treatment electrodes includes implanting the midplane treatment electrodes under skin of the head.

Inventive concept 234. The method according to inventive concept 222, wherein disposing the lateral treatment electrodes includes implanting the lateral treatment electrodes under an arachnoid mater of the subject.

Inventive concept 235. The method according to inventive concept 234, wherein disposing the lateral treatment electrodes includes disposing the lateral treatment electrodes between 1 and 3 cm of the sagittal midplane of the skull.

Inventive concept 236. The method according to inventive concept 234, wherein disposing the lateral treatment electrodes includes disposing the lateral treatment electrodes in the subarachnoid space.

Inventive concept 237. The method according to inventive concept 234, wherein disposing the lateral treatment electrodes includes disposing the lateral treatment electrodes in gray or white matter of a brain of the subject.

Inventive concept 238. The method according to inventive concept 222, wherein disposing the midplane treatment electrodes includes disposing the midplane treatment electrodes within 10 mm of the sagittal midplane of the skull.

Inventive concept 239. The method according to inventive concept 222, wherein disposing the midplane treatment electrodes includes disposing at least five midplane treatment electrodes over the superior sagittal sinus.

Inventive concept 240. The method according to inventive concept 239, wherein disposing the lateral treatment electrodes includes disposing at least five lateral treatment electrodes between 1 and 12 cm of the sagittal midplane of the skull.

Inventive concept 241. The method according to inventive concept 240, wherein disposing the midplane treatment electrodes includes disposing a midplane lead outside the skull, and wherein the midplane treatment electrodes are disposed along the midplane lead, and wherein disposing the lateral treatment electrodes includes disposing a lateral lead within 1 and 12 cm of the sagittal midplane of the skull, and wherein the lateral treatment electrodes are disposed along the lateral lead.

Inventive concept 242. The method according to inventive concept 222, wherein the lateral treatment electrodes include left lateral treatment electrodes and right lateral treatment electrodes, and wherein disposing the lateral treatment electrodes includes disposing the left lateral treatment electrodes left of the sagittal midplane of the skull, and disposing the right lateral treatment electrodes right of the sagittal midplane of the skull.

Inventive concept 243. The method according to inventive concept 242, wherein disposing the left lateral treatment electrodes includes disposing the left lateral treatment electrodes such that at least one of the left lateral treatment electrodes is at least 1 cm from another one of the left lateral treatment electrodes, and wherein disposing the right lateral treatment electrodes includes disposing the right lateral treatment electrodes such that at least one of the right lateral treatment electrodes is at least 1 cm from another one of the right lateral treatment electrodes.

Inventive concept 244. The method according to inventive concept 242, wherein activating the control circuitry to apply the one or more treatment currents between (a) one or more of the midplane treatment electrodes and (b) one or more of the lateral treatment electrodes includes activating the control circuitry to apply:

a first treatment current between a first one of the midplane treatment electrodes and a first one of the left lateral treatment electrodes, a second treatment current between the first one of the midplane treatment electrodes and a first one of the right lateral treatment electrodes, a third treatment current between a second one of the midplane treatment electrodes and a second one of the left lateral treatment electrodes, and a fourth treatment current between the second one of the midplane treatment electrodes and a second one of the right lateral treatment electrodes.

Inventive concept 245. The method according to inventive concept 222, wherein electroosmotically driving the fluid includes:

detecting, by the control circuitry, a voltage difference between the subarachnoid space and the superior sagittal sinus; and setting, by the control circuitry, a level of the one or more treatment currents responsively to the detected voltage difference.

Inventive concept 246. The method according to inventive concept 222, wherein activating the control circuitry includes activating the control circuitry to apply the one or more treatment currents as direct currents.

Inventive concept 247. The method according to inventive concept 246, wherein activating the control circuitry includes activating the control circuitry to apply the one or more direct currents as a plurality of pulses.

The present invention will be more fully understood from the following detailed description of embodiments thereof, taken together with the drawings, in which:

DETAILED DESCRIPTION OF APPLICATIONS

Figure 1A:
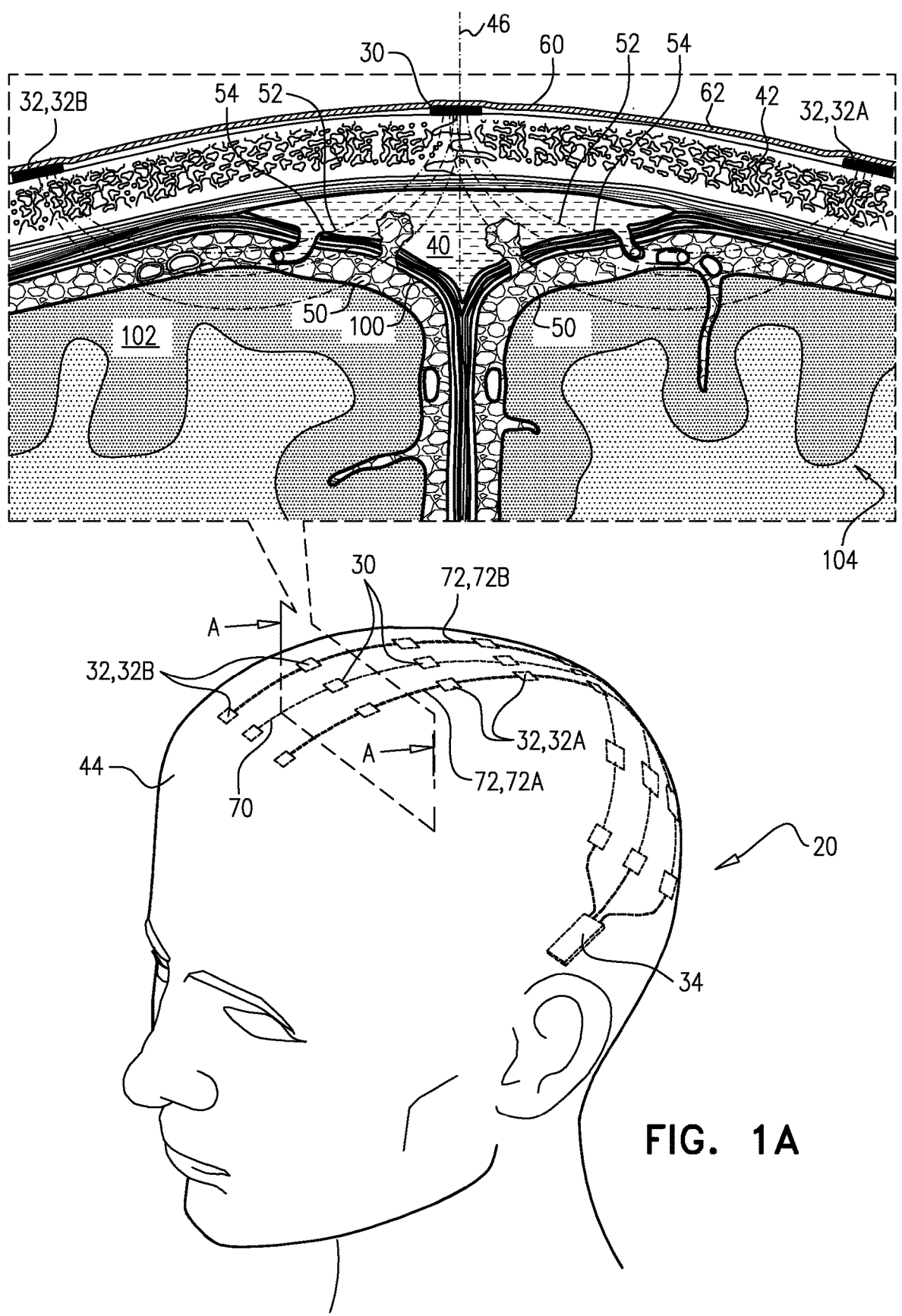
FIGS. 1A-B are schematic illustration of a system for treating Alzheimer's disease, in accordance with respective applications of the present invention.
Figure 1B:
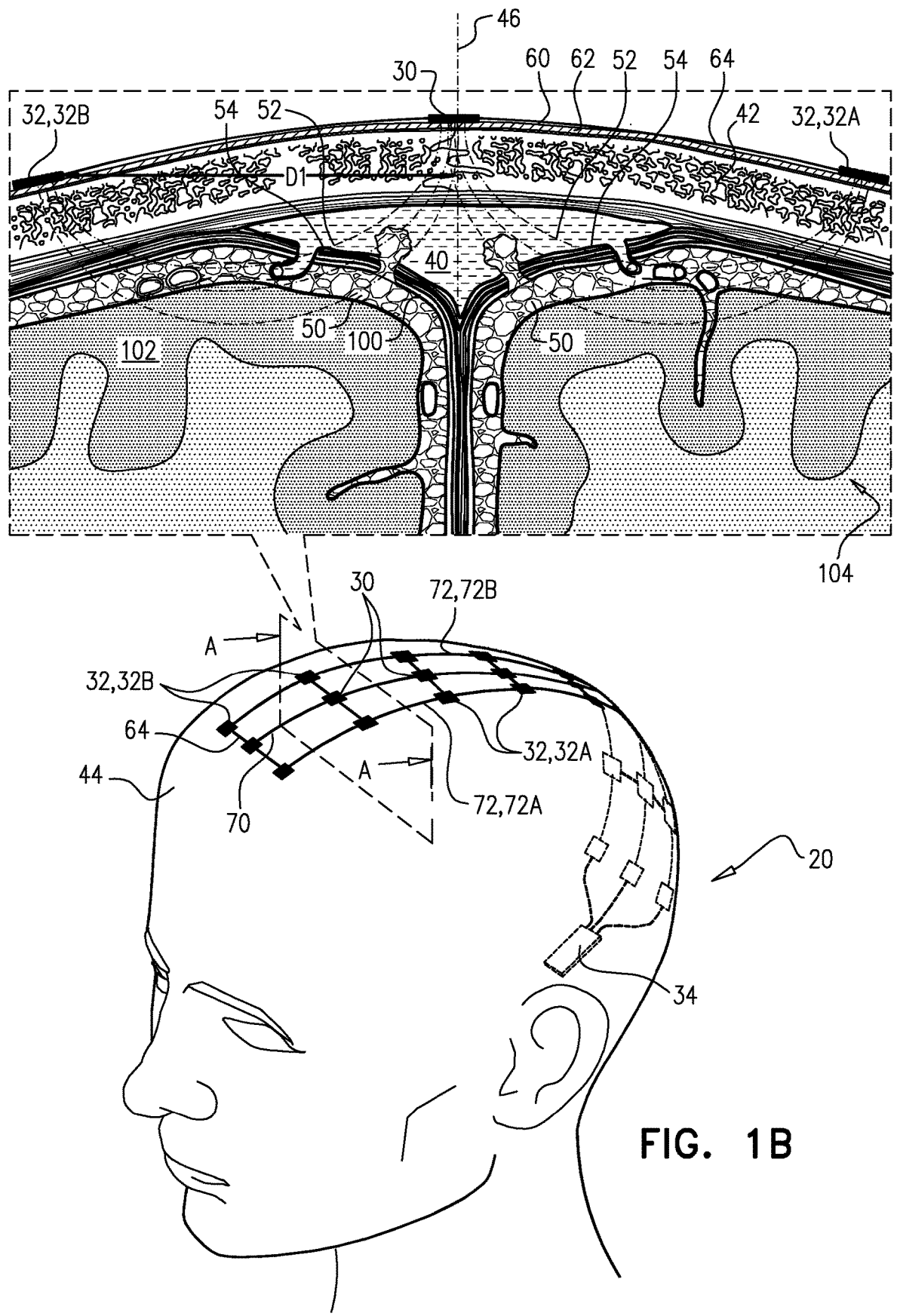

FIGS. 1A-B are schematic illustration of a system 20 for treating Alzheimer's disease, in accordance with respective applications of the present invention. System 20 comprises a plurality of midplane treatment electrodes 30, such as at least 5, no more than 20, and/or between 5 and 20 midplane treatment electrodes 30. System 20 further comprises a plurality of lateral treatment electrodes 32, such as at least 5, no more than 40, and/or between 5 and 40 lateral treatment electrodes 32, such as between 5 and 20 lateral treatment electrodes 32, or between 10 and 40 lateral treatment electrodes. For some applications, the number of each type of treatment electrode is determined based on the size of the head of the subject. For some applications, system 20 comprises twice as many lateral treatment electrodes 32 as midplane treatment electrodes 30. System 20 further comprises control circuitry 34, which is electrically coupled to the treatment electrodes.

For some applications, a method for treating Alzheimer's disease comprises:
  disposing midplane treatment electrodes 30 over a superior sagittal sinus 40, outside and in electrical contact with a skull 42 of a head 44 of a subject identified as at risk of or suffering from Alzheimer's disease;
  disposing lateral treatment electrodes 32 at a distance D1 of between 1 and 12 cm of a sagittal midplane 46 of skull 42 (labeled in FIG. 1B; distance D1 is measured in a straight line from a closest portion of each treatment electrode to sagittal midplane 46, rather than along the curvature of skull 42); and
  treating the subject by electroosmotically driving fluid from a subarachnoid space 50 to superior sagittal sinus 40, by activating control circuitry 34 to apply one or more treatment currents between (a) one or more of midplane treatment electrodes 30 and (b) one or more of lateral treatment electrodes 32 (each of the treatment currents is schematically illustrated in the figures by a plurality of current lines 52).

As used in the present application, including in the claims, "over the superior sagittal sinus" means aligned with the superior sagittal sinus at a location more superficial than the superior sagittal sinus, i.e., at a greater distance from a center of the head. As used in the present application, including in the claims, "treating" includes both treating a subject already diagnosed with a disease, as well as preventing the development of the disease in a subject not diagnosed with the disease and/or asymptomatic for the disease (for example, the disease may be Alzheimer's disease, cerebral amyloid angiopathy (CAA), or hydrocephalus).

For some applications, treating the subject comprises facilitating clearance of amyloid beta from subarachnoid space 50 to superior sagittal sinus 40 by electroosmotically driving the fluid from subarachnoid space 50 to superior sagittal sinus 40. Alternatively or additionally, for some applications, treating the subject comprises facilitating clearance of metal ions from subarachnoid space 50 to superior sagittal sinus 40 by electroosmotically driving the fluid from subarachnoid space 50 to superior sagittal sinus 40. Application of the treatment currents causes a potential difference between subarachnoid space 50 and superior sagittal sinus 40, which causes movement of the amyloid beta and/or metal ions from subarachnoid space 50 to superior sagittal sinus 40.

For some applications, the one or more treatment currents applied using midplane treatment electrodes 30 and lateral treatment electrodes 32 pass between subarachnoid space 50 and superior sagittal sinus 40, via inferolateral surfaces 54 of superior sagittal sinus 40. For some of these applications, at least 40%, e.g., at least 75% or at least 90%, of the treatment currents pass between subarachnoid space 50 and superior sagittal sinus 40, via inferolateral surfaces 54 of superior sagittal sinus 40. For the applications described immediately above, the locations of midplane treatment electrodes 30 and/or lateral treatment electrodes 32 are typically selected such that the one or more treatment currents pass through inferolateral surfaces 54. For example, for configurations in which lateral treatment electrodes 32 are disposed outside and in electrical contact with skull 42, such as described with reference to FIGS. 1A-B, lateral treatment electrodes 32 may be disposed at distance D1 of least 4 cm, no more than 12 cm, and/or between 4 and 12 cm of sagittal midplane 46 of skull 42; for configurations in which lateral treatment electrodes 32 are implanted under an arachnoid mater 100 of the subject, such as described with reference to FIG. 2, lateral treatment electrodes 32 may be disposed at least 1 cm, no more than 3 cm, and/or between 1 and 3 cm of sagittal midplane 46 of skull 42.

For some applications, control circuitry 34 is activated to configure midplane treatment electrodes 30 as cathodes, and lateral treatment electrodes 32 as anodes. This electrical polarity electroosmotically drives fluid from subarachnoid space 50 to superior sagittal sinus 40, which may treat:
  Alzheimer's disease and/or cerebral amyloid angiopathy (CAA) by clearing amyloid beta from subarachnoid space 50 to superior sagittal sinus 40;
  alternatively or additionally, increased flow of cerebrospinal fluid (CSF) out of the brain's ventricular system via subarachnoid space 50 may itself treat Alzheimer's disease and/or CAA, independent of any direct clearance of beta amyloid in the CSF flow; and/or
  hydrocephalus, by driving cerebrospinal fluid (CSF) out of the brain's ventricular system via subarachnoid space 50.

Alternatively, for some applications, control circuitry 34 is activated to configure midplane treatment electrodes 30 as anodes, and lateral treatment electrodes 32 as cathodes. This electrical polarity electrophoretically drives amyloid beta from subarachnoid space 50 to superior sagittal sinus 40, which may treat Alzheimer's disease and/or cerebral amyloid angiopathy (CAA) by clearing amyloid beta from subarachnoid space 50 to superior sagittal sinus 40. In experiments conducted on behalf of the inventor, amyloid beta was found to be attracted to the positive electrode (anode). Alternatively or additionally, this electrical polarity may be used for electroosmotically driving fluid from superior sagittal sinus 40 to subarachnoid space 50.

For some applications, at least five midplane treatment electrodes 30 are disposed over superior sagittal sinus 40. Alternatively or additionally, for some applications, at least five lateral treatment electrodes 32 between 1 and 12 cm of sagittal midplane 46 of skull 42. For some applications, each of lateral treatment electrodes 32 is disposed between 1 and 12 cm of at least one of midplane treatment electrodes 30.

For some applications, midplane treatment electrodes 30 are disposed within 10 mm of sagittal midplane 46 of skull 42. Alternatively or additionally, for some applications, midplane treatment electrodes 30 are disposed such that at least one of midplane treatment electrodes 30 is at least 5 mm from another one of midplane treatment electrodes 30, no more than 20 mm from another one of midplane treatment electrodes 30, and/or between 5 and 30 mm from another one of midplane treatment electrodes 30. For some applications, at least one of lateral treatment electrodes 32 is disposed is at least 5 mm from another one of lateral treatment electrodes 32.

For some applications, such as shown in FIG. 1A, midplane treatment electrodes 30 are implanted under skin 62 of head 44. For other applications, such as shown in FIG. 1B, midplane treatment electrodes 30 are disposed outside head 44, such as on an external surface 60 of head 44. For some applications, system 20 further comprises a midplane lead 70, along which midplane treatment electrodes 30 are disposed (e.g., fixed). Midplane lead 70 is disposed outside skull 42 in order to dispose midplane treatment electrodes 30 over superior sagittal sinus 40. For some applications in which midplane treatment electrodes 30 are implanted under skin 62, the implantation is performed by introducing midplane lead 70 through an incision in skin 62, typically at a posterior site of the head, and tunneling the midplane lead toward an anterior site of the head, such as near the forehead. Optionally, each of midplane treatment electrodes 30 is inserted through a respective incision in skin 62, and connected to midplane lead 70.

For some applications, the method further comprises implanting control circuitry 34 under skin of the subject, such as under skin 62 of head 44, or elsewhere in the subject's body.

For some applications, such as shown in FIGS. 1A-B, lateral treatment electrodes 32 are disposed outside and in electrical contact with skull 42. For some of these applications, lateral treatment electrodes 32 are implanted under skin 62 of head 44, such as shown in FIG. 1A. Alternatively, lateral treatment electrodes 32 are disposed outside head 44, such as on external surface 60 of head 44, such as shown in FIG. 1B. For some of these applications, lateral treatment electrodes 32 may be disposed at least 4 cm, no more than 12 cm, and/or between 4 and 12 cm of sagittal midplane 46 of skull 42. (As used in the present application, including in the claims, all specified ranges include their endpoints.) Such positioning may generate one or more treatment currents that pass between subarachnoid space 50 and superior sagittal sinus 40, via inferolateral surfaces 54 of superior sagittal sinus 40, as described above. For some applications, system 20 further comprises a lateral lead 72, along which lateral treatment electrodes 32 are disposed (e.g., fixed). Lateral lead 72 is disposed outside skull 42, typically within 1 and 12 cm of sagittal midplane 46 of skull 42, in order to dispose lateral treatment electrodes 32. For some applications in which lateral treatment electrodes 32 are implanted under skin 62, the implantation is performed by introducing lateral lead 72 through an incision in skin 62, typically at a posterior site of the head, and tunneling the lateral lead toward an anterior site of the head, such as near the forehead. Optionally, each of lateral treatment electrodes 32 is inserted through a respective incision in skin 62, and connected to lateral lead 72. For some applications, instead of providing lateral lead 72, lateral treatment electrodes 32 are instead coupled to midplane lead 70. Midplane lead 70 is introduced with the lateral electrodes constrained, and, the lateral electrodes are configured upon release to extend laterally, typically automatically. This configuration may also be used for applications in which both left and right lateral electrodes are provided, as described hereinbelow.

For some applications, control circuitry 34 is activated to independently apply the treatment currents between respective pairs of midplane treatment electrodes 30 and lateral treatment electrodes 32. Such independent application of the currents allows continued effective operation of system 20 even if a low resistance should develop between the electrodes of one of the pairs (e.g., because of anatomical variations). For some of these applications, in order to enable such independent application of the currents, midplane lead 70 comprises a plurality of conductive wires corresponding to a number of midplane treatment electrodes 30, and lateral lead 72 comprises a plurality of conductive wires corresponding to a number of lateral treatment electrodes 32. Alternatively, control circuitry 34 and the electrodes implement electrical multiplexing, as is known in the art, in which case each of the leads need only comprise a single conductive wire. Alternatively, for some applications, all of midplane treatment electrodes 30 are electrically coupled to one another (such as by a single conductive wire in the midplane lead), and all of lateral treatment electrodes 32 are electrically coupled to one other (such as by a single conductive wire in the lateral lead).

For some applications of the configuration shown in FIG. 1B, system 20 further comprises one or more thin elongate support elements 64, which couple lateral leads 72 to midplane lead 70, in order to provide proper spacing and alignment between the midplane electrodes and the lateral electrodes. Support elements 64 are typically non-conductive.

For some applications, control circuitry 34 is configured to apply the one or more treatment currents with an average amplitude of between 1 and 3 milliamps. (The resulting voltage is typically greater in the configuration shown in FIGS. 1A-B than in the configuration shown in FIG. 2, because the one or more treatment currents pass through skull 42 twice.)

For some applications, control circuitry 34 is activated to apply the one or more treatment currents as direct current, typically as a plurality of pulses, for example at greater than 500 Hz and/or less than 2 kHz, e.g., at 1 kHz. For some applications, a duty cycle of the pulses is above 90%, and for some applications pulses are not used but instead an effective duty cycle of 100% is utilized. Typically, but not necessarily, the duty cycle is 90% or lower, because a given level of applied voltage produces higher current in the tissue if the capacitance in the tissue is allowed to discharge between pulses. For other applications, control circuitry 34 is activated to apply the one or more treatment currents as alternating current with a direct current offset and a constant polarity. For example, the frequency may be at least 1 Hz, no more than 100 Hz (e.g., no more than 10 Hz), and/or between 1 Hz and 100 Hz (e.g., between 1 Hz and 10 Hz).

For some applications, control circuitry 34 is activated to apply the one or more treatment currents in sessions, each of which has a duration of several seconds or several minutes, or continuously for longer periods (e.g., 30 minutes). For some applications, the one or more treatment currents are not applied for a period that is at least an hour. Optionally, control circuitry 34 is activated to apply the one or more treatment currents only when the subject is sleeping, such as to inhibit any sensations that may be associated with application of the one or more treatment currents. For example, control circuitry 34 may be activated to use one or more of the electrodes as EEG electrodes to detect sleep. For some applications, power for activating and/or charging control circuitry 34 is transmitted from a wireless energy transmitter in a hat, such as described hereinbelow with reference to FIG. 3, or from a wireless energy transmitter in, under, or above a mattress. For some applications, control circuitry 34 is activated to apply the one or more treatment currents according to a pre-selected schedule, such as a duty cycle, such as for a few hours per day. For example, control circuitry 34 may be configured to be controlled and/or powered by an extracorporeal control circuitry, such as a control circuitry comprising a wireless transmitter, disposed in and/or in the vicinity of the subject's bed. For some applications, one or more rest periods during which the treatment voltage is not applied are provided in the pre-selected schedule.

For some applications, lateral treatment electrodes 32 comprise left lateral treatment electrodes 32A and right lateral treatment electrodes 32B. Left lateral treatment electrodes 32A are disposed left of sagittal midplane 46 of skull 42, and right lateral treatment electrodes 32B are disposed right of sagittal midplane 46 of skull 42. For some applications, control circuitry 34 is activated to configure midplane treatment electrodes 30 as cathodes, and left and right lateral treatment electrodes 32A and 32B as left and right anodes, respectively.

For some applications, left lateral treatment electrodes 32A are disposed such that at least one of left lateral treatment electrodes 32A is at least 1 cm, no more than 5 cm, and/or between 1 and 5 cm (e.g., 3 cm) from another one of left lateral treatment electrodes 32A, and/or right lateral treatment electrodes 32B are disposed such that at least one of right lateral treatment electrodes 32B is at least 1 cm, no more than 5 cm, and/or between 1 and 5 cm (e.g., 3 cm) from another one of right lateral treatment electrodes 32B. Alternatively or additionally, for some applications, left lateral treatment electrodes 32A are disposed such that longitudinally-adjacent ones of the electrodes are disposed at least 1 cm, no more than 5 cm, and/or between 1 and 5 cm (e.g., 3 cm) from each other, and/or right lateral treatment electrodes 32B are disposed such that longitudinally-adjacent ones of the electrodes are disposed at least 1 cm, no more than 5 cm, and/or between 1 and 5 cm (e.g., 3 cm) from each other. For some applications, at least five left lateral treatment electrodes 32A are disposed left of sagittal midplane 46 of skull 42, and/or at least five right lateral treatment electrodes 32B are disposed right of sagittal midplane 46 of skull 42.

As mentioned above, for some applications, system 20 further comprises midplane lead 70, along which midplane treatment electrodes 30 are disposed (e.g., fixed). Midplane lead 70 is disposed outside skull 42 in order to dispose midplane treatment electrodes 30. For some of these applications, system 20 further comprises (a) a left lateral lead 72A, along which left lateral treatment electrodes 32A are disposed (e.g., fixed), and (b) a right lateral lead 72B, along which right lateral treatment electrodes 32B are disposed (e.g., fixed). Left lateral lead 72A is disposed outside skull 42, typically within 1 and 12 cm of sagittal midplane 46 of skull 42, in order to dispose left lateral treatment electrodes 32A. Right lateral lead 72B is disposed outside skull 42, typically within 1 and 12 cm of sagittal midplane 46 of skull 42, in order to dispose right lateral treatment electrodes 32B.

For some applications, control circuitry 34 is activated to independently apply the treatment currents between respective pairs of midplane and left lateral treatment electrodes 30 and 32A, and between respective pairs of midplane and right lateral treatment electrodes 30 and 32B. For example, control circuitry 34 may be activated to apply the treatment currents between each of the midplane treatment electrodes 30 and both (a) a corresponding one of left lateral treatment electrodes 32A and (b) a corresponding one of right lateral treatment electrodes 32B. For some of these applications, in order to enable such independent application of the treatment currents, midplane lead 70 comprises a plurality of conductive wires corresponding to a number of midplane treatment electrodes 30, left lateral lead 72A comprises a plurality of conductive wires corresponding to a number of left lateral treatment electrodes 32A, and right lateral lead 72B comprises a plurality of conductive wires corresponding to a number of right lateral treatment electrodes 32B. Alternatively, control circuitry 34 and the electrodes implement electrical multiplexing, as is known in the art, in which case each of the leads need only comprise a single conductive wire. Alternatively, for some applications, all of midplane treatment electrodes 30 are electrically coupled to one other (such as by a single conductive wire in the midplane lead), all of left lateral treatment electrodes 32A are electrically coupled to one other (such as by a single conductive wire in the left lateral lead), and all of right lateral treatment electrodes 32B are electrically coupled to one other (such as by a single conductive wire in the right lateral lead).

For example, control circuitry 34 may be activated to apply:
  a first treatment current between a first one of midplane treatment electrodes 30 and a first one of left lateral treatment electrodes 32A,
  a second treatment current between the first one of midplane treatment electrodes 30 and a first one of right lateral treatment electrodes 32B,
  a third treatment current between a second one of midplane treatment electrodes 30 and a second one of left lateral treatment electrodes 32A, and
  a fourth treatment current between the second one of midplane treatment electrodes 30 and a second one of right lateral treatment electrodes 32B.

Typically, control circuitry 34 is activated to configure midplane treatment electrodes 30 as cathodes, and left and right lateral treatment electrodes 32A and 32B as left and right anodes, respectively.

Figure 2:
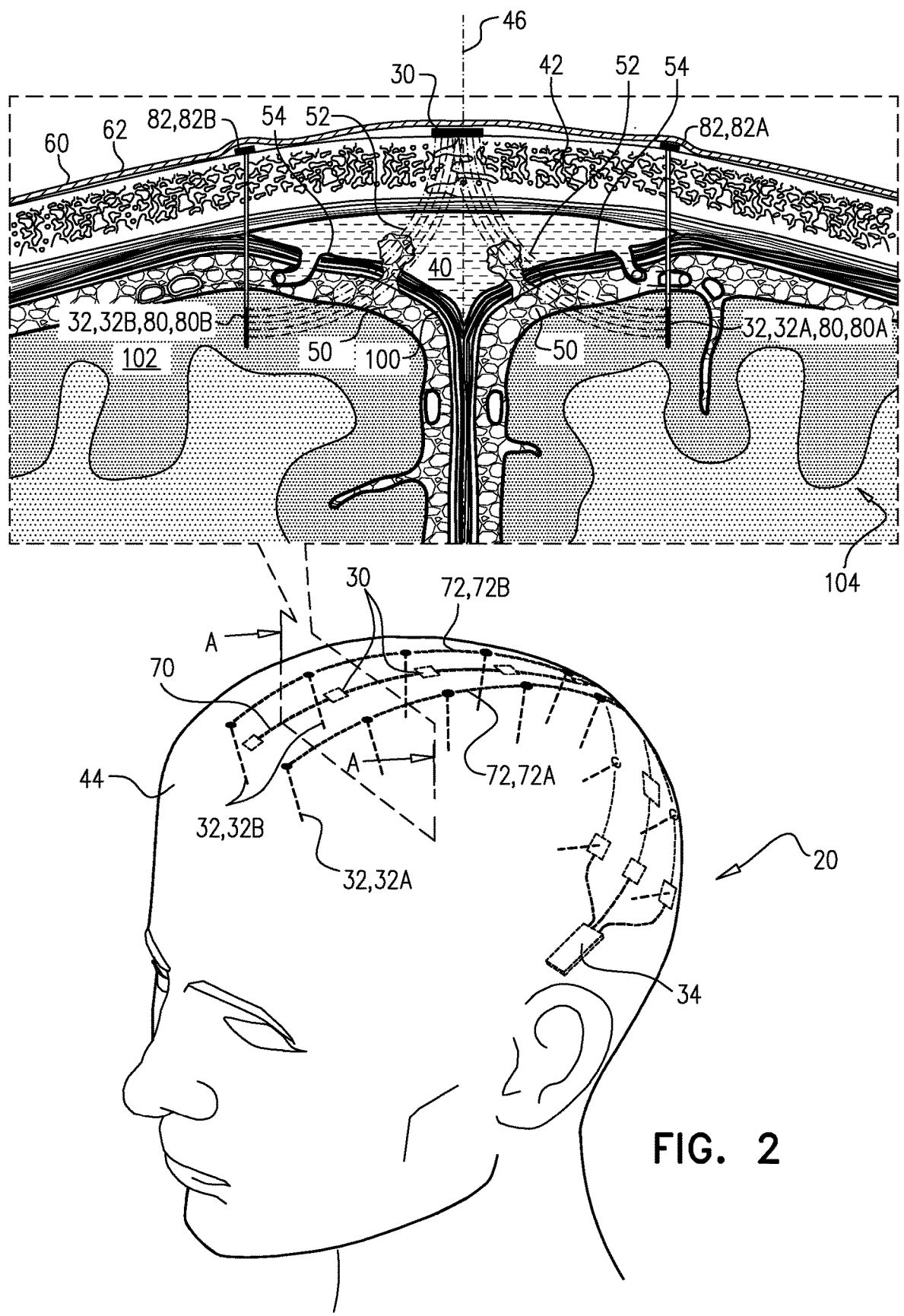
FIG. 2 is a schematic illustration of another configuration of the system of FIGS. 1A-B, in accordance with an application of the present invention.

Reference is now made to FIG. 2, which is a schematic illustration of another configuration of system 20, in accordance with an application of the present invention. In this configuration, lateral treatment electrodes 32 comprise lateral sub-arachnoid-mater treatment electrodes 80, which are implanted under arachnoid mater 100 of the subject, such as in subarachnoid space 50, in gray matter 102, or in white matter of a brain 104 of the subject. For example, lateral treatment sub-arachnoid-mater electrodes 80 may comprise needle electrodes, as is known in the art; optionally, lateral treatment sub-arachnoid-mater electrodes 80 comprise respective proximal anchors 82. This configuration may implement any of the techniques described hereinabove with reference to FIGS. 1A-B, mutatis mutandis.

For some of these applications, lateral sub-arachnoid-mater treatment electrodes 80 are disposed at least 1 cm, no more than 3 cm, and/or between 1 and 3 cm of sagittal midplane 46 of skull 42. Such positioning may generate the treatment currents that pass between subarachnoid space 50 and superior sagittal sinus 40, via inferolateral surfaces 54 of superior sagittal sinus 40, as described above. For some applications, each of lateral sub-arachnoid-mater treatment electrodes 80 is disposed between 1 and 3 cm of at least one of midplane treatment electrodes 30. For some applications, each of lateral sub-arachnoid-mater treatment electrodes 80 is disposed between 1 and 3 cm of one of midplane treatment electrodes 30 that is closest to the lateral treatment electrode.

For some applications, a surgical technique for implanting lateral lead 72 comprises:
- drilling a hole through skull 42, typically at a posterior site of the skull, and typically between 1 and 3 cm of sagittal midplane 46 of skull 42;
- introducing a catheter through the hole and into subarachnoid space 50 or the gray or white matter of the brain, while a lateral lead 72 is disposed along the catheter;
- advancing the catheter within the brain to a more anterior site, such as near the forehead; and
- withdrawing the catheter while leaving lateral lead 72 in place within the brain.

Lateral lead 72 is then electrically coupled to control circuitry 34, if not previously coupled prior to the implantation procedure.

This procedure is typically performed twice, once for each of left and right lateral leads 72A and 72B. Therefore, only two holes need to be made through the skull in order to implant all of lateral sub-arachnoid-mater treatment electrodes 80. A similar procedure may be employed for implanting midplane lead 70 under skin 62; alternatively, midplane lead 70 is implanted without the use of a catheter, such as by tunneling, as described hereinabove with reference to FIG. 1A.

Figure 3:
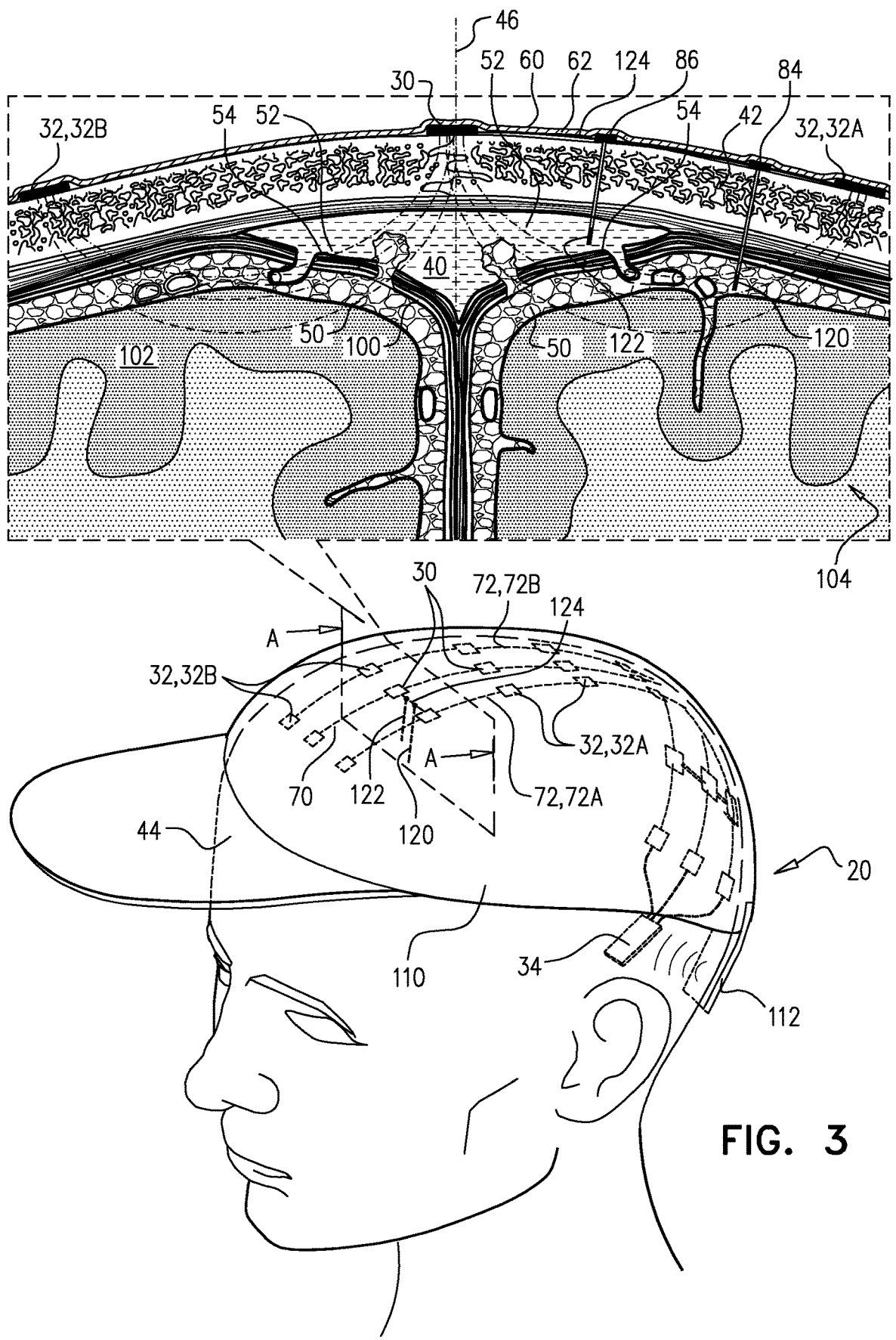
FIG. 3 is a schematic illustration of yet another configuration of the system of FIG. 1A, in accordance with an application of the present invention.

Reference is now made to FIG. 3, which is a schematic illustration of yet another configuration of system 20, in accordance with an application of the present invention. Although this configuration is illustrated for the configuration of system 20 shown in FIG. 1A, it may also be used with the configurations shown in FIGS. 1B and 2. In this configuration, electroosmotically driving the fluid comprises (a) detecting, by control circuitry 34, a voltage difference between subarachnoid space 50 and superior sagittal sinus 40, and (b) setting, by control circuitry 34, a level of the one or more treatment currents responsively to the detected voltage difference. For some applications, such as shown in FIG. 3, system 20 further comprises one or more first detection electrodes, such as a single first detection electrode 120 and one or more second detection electrodes 122, such as a single second detection electrode 122. For some applications, first and second detection electrodes 120 and 122 comprise respective needle electrodes, as is known in the art; optionally, first and second detection electrodes 120 and 122 comprise respective proximal anchors 84 and 86. Single first detection electrode 120 is implanted in subarachnoid space 50, and single second detection electrode 122 is implanted in superior sagittal sinus 40. For some applications, detecting the voltage difference comprises detecting, by control circuitry 34, the voltage difference between first and second detection electrodes 120 and 122.

Reference is now made to FIGS. 2 and 3. For some applications, control circuitry 34 is activated to detect the voltage difference between at least one of midplane treatment electrodes 30 and at least one of lateral treatment electrodes 32. For some of these applications, lateral treatment electrodes 32 are disposed outside and in electrical contact with skull 42, such as described hereinabove with reference to FIGS. 1A-B, while for others of these applications, lateral treatment electrodes 32 comprise lateral sub-arachnoid-mater treatment electrodes 80, which are implanted under arachnoid mater 100 of the subject, such as in subarachnoid space 50, in gray matter 102, or in white matter of a brain 104 of the subject, as described hereinabove with reference to FIG. 2.

For other applications, control circuitry 34 is activated to detect the voltage difference between second detection electrode 122 and at least one of lateral treatment electrodes 32. For some of these applications, lateral treatment electrodes 32 are disposed outside and in electrical contact with skull 42, such as described hereinabove with reference to FIGS. 1A-B, while for others of these applications, lateral treatment electrodes 32 comprise lateral sub-arachnoid-mater treatment electrodes 80, which are implanted under arachnoid mater 100 of the subject, such as in subarachnoid space 50, in gray matter 102, or in white matter of a brain 104 of the subject, as described hereinabove with reference to FIG. 2.

For still other applications, control circuitry 34 is activated to detect the voltage difference between at least one of midplane treatment electrodes 30 and first detection electrode 120.

Reference is still made to FIG. 3. For some applications, system 20 further comprises a hat 110, which comprises a wireless energy transmitter 112. When the subject wears the hat, transmitter 112 is disposed in a vicinity of control circuitry 34 (which may be implanted subcutaneously, as described above). Control circuitry 34 comprises a wireless energy receiver to receive energy transmitted by transmitter 112. Although described with reference to FIG. 3, hat 110 may also be implemented in combination with any of the other configurations of system 20 described herein, including those shown in FIGS. 1A, 1B, and 2.

Figure 4:
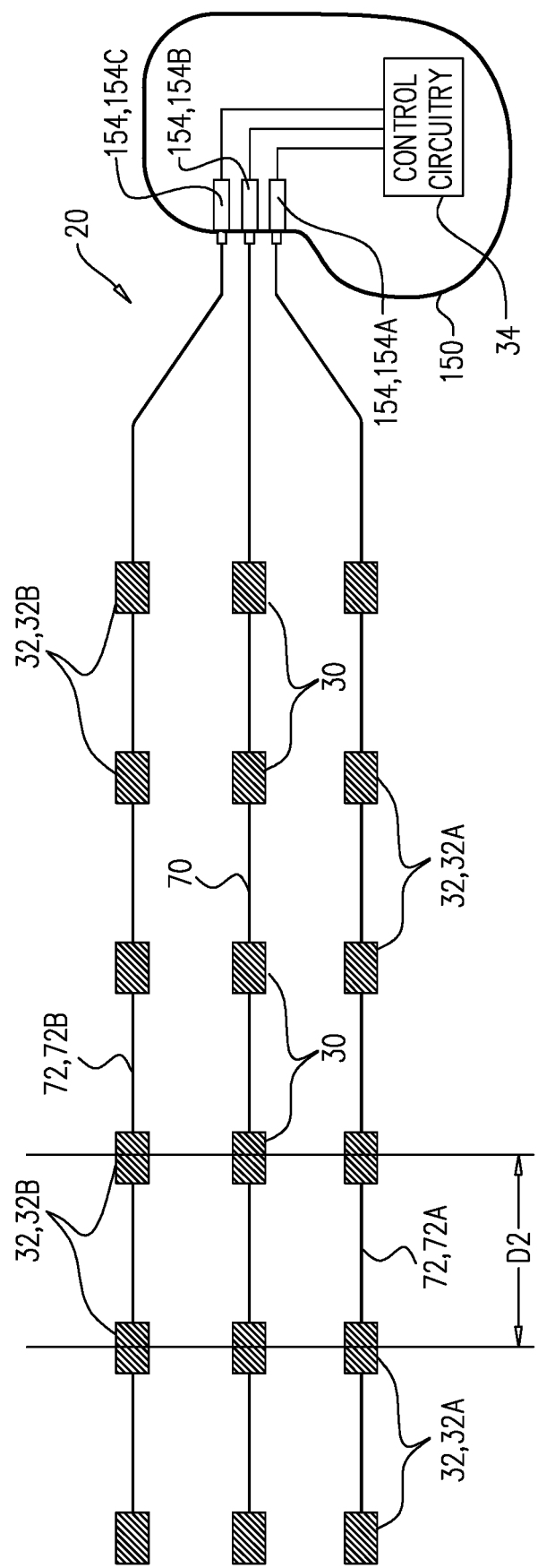
FIG. 4 is a schematic illustration of yet another configuration of the system of FIG. 1A, in accordance with an application of the present invention.

Reference is now made to FIG. 4, which is a schematic illustration of system 20, in accordance with an application of the present invention. For some applications, system 20 comprises a housing 150, which contains control circuitry 34. For some applications, housing 150 is implantable, such as subcutaneous; for example, the housing may be similar to conventional pacemaker housings ("cans"). For some applications, housing 150 comprises first, second, and third lead interfaces 154A, 154B, and 154C, for electrical and mechanical coupling with midplane lead 70 and lateral leads 72. For example, first, second, and third lead interfaces 154A, 154B, and 154C may comprise first, second, and third ports, into which corresponding connectors of the leads are inserted. Alternatively, the leads may have hardwired connections with the lead interfaces. First, second, and third lead interfaces 154A, 154B, and 154C are also electrically coupled with control circuitry 34.

Typically, the lead interfaces are physically arranged such that second lead interface 154B is between first and third lead interfaces 154A and 154C on housing 150. Control circuitry 34 is configured to apply current through second lead interface 154B to midplane lead 70 such that midplane treatment electrodes 30 are cathodes, and to apply current through first and third lead interfaces 154A and 154B such that lateral treatment electrodes 32 are anodes.

Alternatively, for some applications, housing 150 comprises only two lead interfaces, and left and right lateral leads 72A and 72B are electrically coupled to each other so as define a single, joint connector, which is coupleable to one of the lead interfaces of the housing.

As mentioned above with reference to FIGS. 1A-B, for some applications system 20 comprises between 5 and 20 midplane treatment electrodes 30, a corresponding number of left lateral treatment electrodes 32A, and a corresponding number of right lateral treatment electrodes 32B. For some applications, an average distance D2 between (a) longitudinally-adjacent pairs of midplane treatment electrodes 30, (b) longitudinally-adjacent pairs of first lateral treatment electrodes 32A, and (c) longitudinally-adjacent pairs of second lateral treatment electrodes 32B is at least 1 cm, no more than 5 cm, and/or between 1 and 5 cm (e.g., 3 cm), measured between longitudinal midpoints of the electrodes. For some applications, each of midplane lead 70, left lateral lead 72A, and right lateral lead 72B, when fully extended, has a length of at least 10 cm, no more than 40 cm (e.g., no more than 30 cm), and/or between 10 and 40 cm (e.g., between 10 and 30 cm).

For some applications, system 20 comprises:
- exactly three leads, consisting of a midplane lead 70, a left lateral lead 72A, and a right lateral lead 72B;
- at least five midplane treatment electrodes 30, which are disposed (e.g., fixed) along midplane lead 70 at an average distance of at least 1 cm, no more than 5 cm, and/or between 1 and 5 cm (e.g., 3 cm) between longitudinally-adjacent pairs of midplane treatment electrodes 30, measured between longitudinal midpoints of midplane treatment electrodes 30;
- at least five left lateral treatment electrodes 32A, which are disposed (e.g., fixed) along left lateral lead 72A at an average distance of at least 1 cm, no more than 5 cm, and/or between 1 and 5 cm (e.g., 3 cm) between longitudinally-adjacent pairs of left lateral treatment electrodes 32A, measured between longitudinal midpoints of left lateral treatment electrodes 32A;
- at least five right lateral treatment electrodes 32B, which are disposed (e.g., fixed) along right lateral lead 72B at an average distance of at least 1 cm, no more than 5 cm, and/or between 1 and 5 cm (e.g., 3 cm) between longitudinally-adjacent pairs of right lateral treatment electrodes 32B, measured between longitudinal midpoints of right lateral treatment electrodes 32B; and
- housing 150, which comprises control circuitry 34, to which midplane treatment electrodes 30, left lateral treatment electrodes 32A, and right lateral treatment electrodes 32B are electrically coupled via midplane lead 70, left lateral lead 72A, and right lateral lead 72B, respectively.

Control circuitry 34 is configured to:
- configure midplane treatment electrodes 30 as cathodes, and left and right lateral treatment electrodes 32A and 32B as left and right anodes, respectively,
- apply respective treatment currents between (a) (i) one or more of midplane treatment electrodes 30 and (ii) one or more of left lateral treatment electrodes 32A, and (b) (i) one or more of midplane treatment electrodes 30 and (ii) one or more of right lateral treatment electrodes 32B, and
- configure the treatment currents to treat the subject by electroosmotically driving fluid from subarachnoid space 50 to superior sagittal sinus 40.

Reference is made to FIGS. 1A-4. For any of the applications described herein, system 20 may comprise:
- a single midplane treatment electrode 30, rather than a plurality of midplane treatment electrodes 30,
- a single lateral treatment electrode 32, rather than a plurality of lateral treatment electrodes 32,
- a single left lateral treatment electrode 32A, rather than a plurality of left lateral treatment electrodes 32A, and/or
- a single right lateral treatment electrode 32B, rather than a plurality of right lateral treatment electrodes 32B.

For some of these applications, any of these single electrodes comprises an elongate electrode having a length of at least 10 cm, no more than 40 cm (e.g., no more than 30 cm), and/or between 10 and 40 cm (e.g., between 10 and 30 cm); for example, the elongate electrode may comprise an electrically-non-insulated wire.

Although the techniques described hereinabove have been described as treating the subject by electroosmotically driving fluid from subarachnoid space 50 to superior sagittal sinus 40, the techniques may alternatively or additionally be used without electroosmosis.

Reference is made to FIGS. 1A-4. In some applications of the present invention, the techniques described herein are alternatively or additionally used to treat cerebral amyloid angiopathy (CAA).

Reference is still made to FIGS. 1A-4. In some applications of the present invention, the techniques described herein are alternatively or additionally used to treat hydrocephalus, by driving cerebrospinal fluid (CSF) out of the brain's ventricular system via subarachnoid space 50. For some of these applications, such as for treating normal pressure hydrocephalus, in order to prevent an excessive reduction in pressure and/or overdrainage of CSF, control circuitry 34 is configured to measure CSF pressure and/or, via two or more electrodes in electrically contact with the CSF, CSF impedance (to monitor the volume of CSF) in the brain's ventricular system. For some applications, control circuitry 34 implements an algorithm that balances between CSF pressure and CSF impedance, optionally using fuzzy logic.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An electrical amyloid beta-clearance system for treating a subject identified as at risk of or suffering from Alzheimer's disease, the system comprising:
   - midplane treatment electrodes, adapted to be disposed over a superior sagittal sinus, outside and in electrical contact with a skull of a head of the subject;
   - lateral treatment electrodes, adapted to be disposed between 1 and 12 cm of a sagittal midplane of the skull; and
   - control circuitry, configured to clear amyloid beta from a subarachnoid space to the superior sagittal sinus, by applying one or more treatment currents between (a) one or more of the midplane treatment electrodes and (b) one or more of the lateral treatment electrodes.

2. The system according to claim 1, wherein the control circuitry is configured to clear the amyloid beta by electrophoretically driving the amyloid beta from the subarachnoid space to the superior sagittal sinus.

3. The system according to claim 2, wherein the control circuitry is configured to configure the midplane treatment electrodes as anodes, and the lateral treatment electrodes as cathodes.

4. The system according to claim 1, wherein the control circuitry is configured to apply the one or more treatment currents with an average amplitude of between 1 and 3 milliamps.

5. The system according to claim 1, wherein the lateral treatment electrodes are adapted to be disposed outside and in electrical contact with the skull.

6. The system according to claim 5, wherein the lateral treatment electrodes are adapted to be disposed between 5 and 12 cm of the sagittal midplane of the skull.

7. The system according to claim 1, wherein the midplane treatment electrodes are adapted to be disposed outside the head.

8. The system according to claim 1, wherein the midplane treatment electrodes are adapted to be implanted under skin of the head.

9. The system according to claim 1, wherein the lateral treatment electrodes are adapted to be implanted under an arachnoid mater of the subject.

10. The system according to claim 1,
wherein the system further comprises (a) a midplane lead, which is adapted to be disposed outside the skull, and (b) a lateral lead, which is adapted to be disposed within 1 and 12 cm of the sagittal midplane of the skull,
wherein the system comprises at least five midplane treatment electrodes that are disposed along the midplane lead, and
wherein the system comprises at least five lateral treatment electrodes that are disposed along the lateral lead.

11. The system according to claim 1, wherein the lateral treatment electrodes comprise:
left lateral treatment electrodes, which are adapted to be disposed left of the sagittal midplane of the skull; and
right lateral treatment electrodes, which are adapted to be disposed right of the sagittal midplane of the skull.

12. The system according to claim 11, wherein the control circuitry is configured to apply the one or more treatment currents between (a) one or more of the midplane treatment electrodes and (b) one or more of the lateral treatment electrodes comprises activating the control circuitry to apply:
a first treatment current between a first one of the midplane treatment electrodes and a first one of the left lateral treatment electrodes,
a second treatment current between the first one of the midplane treatment electrodes and a first one of the right lateral treatment electrodes,
a third treatment current between a second one of the midplane treatment electrodes and a second one of the left lateral treatment electrodes, and
a fourth treatment current between the second one of the midplane treatment electrodes and a second one of the right lateral treatment electrodes.

13. The system according to claim 1, wherein the control circuitry is configured to apply the one or more treatment currents as direct currents.

14. The system according to claim 13, wherein the control circuitry is configured to apply the one or more direct currents as a plurality of pulses.

15. The system according to claim 1, wherein the control circuitry is configured to configure the midplane treatment electrodes as cathodes, and the lateral treatment electrodes as anodes.

16. A method including:
disposing midplane treatment electrodes over a superior sagittal sinus, outside and in electrical contact with a skull of a head of a subject identified as at risk of or suffering from Alzheimer's disease;
disposing lateral treatment electrodes between 1 and 12 cm of a sagittal midplane of the skull; and
treating the subject by clearing amyloid beta from a subarachnoid space to the superior sagittal sinus, by activating control circuitry to apply one or more treatment currents between (a) one or more of the midplane treatment electrodes and (b) one or more of the lateral treatment electrodes.

17. The method according to claim 16, wherein clearing the amyloid beta includes electrophoretically driving the amyloid beta from the subarachnoid space to the superior sagittal sinus.

18. The method according to claim 17, wherein activating the control circuitry includes activating the control circuitry to configure the midplane treatment electrodes as anodes, and the lateral treatment electrodes as cathodes.

19. The method according to claim 16, wherein activating the control circuitry includes activating the control circuitry to apply the one or more treatment currents with an average amplitude of between 1 and 3 milliamps.

20. The method according to claim 16, wherein disposing the lateral treatment electrodes includes disposing the lateral treatment electrodes outside and in electrical contact with the skull.

21. The method according to claim 20, wherein disposing the lateral treatment electrodes includes disposing the lateral treatment electrodes on an external surface of the head.

22. The method according to claim 20, wherein disposing the lateral treatment electrodes includes implanting the lateral treatment electrodes under skin of the head.

23. The method according to claim 20, wherein disposing the lateral treatment electrodes comprises disposing the lateral treatment electrodes between 5 and 12 cm of the sagittal midplane of the skull.

24. The method according to claim 16, wherein disposing the midplane treatment electrodes includes disposing the midplane treatment electrodes outside the head.

25. The method according to claim 16, wherein disposing the midplane treatment electrodes includes implanting the midplane treatment electrodes under skin of the head.

26. The method according to claim 16, wherein disposing the lateral treatment electrodes includes implanting the lateral treatment electrodes under an arachnoid mater of the subject.

27. The method according to claim 26, wherein disposing the lateral treatment electrodes includes disposing the lateral treatment electrodes between 1 and 3 cm of the sagittal midplane of the skull.

28. The method according to claim 26, wherein disposing the lateral treatment electrodes includes disposing the lateral treatment electrodes in the subarachnoid space.

29. The method according to claim 26, wherein disposing the lateral treatment electrodes includes disposing the lateral treatment electrodes in gray or white matter of a brain of the subject.

30. The method according to claim 16,
wherein the lateral treatment electrodes include left lateral treatment electrodes and right lateral treatment electrodes, and
wherein disposing the lateral treatment electrodes includes disposing the left lateral treatment electrodes left of the sagittal midplane of the skull, and disposing the right lateral treatment electrodes right of the sagittal midplane of the skull.

31. The method according to claim 30, wherein activating the control circuitry to apply the one or more treatment currents between (a) one or more of the midplane treatment electrodes and (b) one or more of the lateral treatment electrodes includes activating the control circuitry to apply:
- a first treatment current between a first one of the midplane treatment electrodes and a first one of the left lateral treatment electrodes,
- a second treatment current between the first one of the midplane treatment electrodes and a first one of the right lateral treatment electrodes,
- a third treatment current between a second one of the midplane treatment electrodes and a second one of the left lateral treatment electrodes, and
- a fourth treatment current between the second one of the midplane treatment electrodes and a second one of the right lateral treatment electrodes.

32. The method according to claim 16, wherein activating the control circuitry includes activating the control circuitry to apply the one or more treatment currents as direct currents.

33. The method according to claim 32, wherein activating the control circuitry includes activating the control circuitry to apply the one or more direct currents as a plurality of pulses.

34. The method according to claim 16, wherein activating the control circuitry includes activating the control circuitry to configure the midplane treatment electrodes as cathodes, and the lateral treatment electrodes as anodes.

* * * * *